United States Patent
Lee et al.

(10) Patent No.: US 10,390,748 B2
(45) Date of Patent: Aug. 27, 2019

(54) MONITORING A DRIVER OF A VEHICLE

(71) Applicant: LG ELECTRONICS INC., Seoul (KR)

(72) Inventors: Jaehee Lee, Seoul (KR); Hyeoncheol Lee, Seoul (KR); Kiho Lee, Seoul (KR)

(73) Assignee: LG Electronics Inc., Seoul (KR)

( * ) Notice: Subject to any disclaimer, the term of this patent is extended or adjusted under 35 U.S.C. 154(b) by 774 days.

(21) Appl. No.: 14/676,868

(22) Filed: Apr. 2, 2015

(65) Prior Publication Data

US 2015/0351681 A1 Dec. 10, 2015

Related U.S. Application Data

(60) Provisional application No. 61/983,895, filed on Apr. 24, 2014.

(30) Foreign Application Priority Data

Jun. 5, 2014 (KR) ........................ 10-2014-0068529

(51) Int. Cl.
| | | |
|---|---|---|
| *A61B 5/18* | (2006.01) | |
| *A61B 5/00* | (2006.01) | |
| *A61B 5/11* | (2006.01) | |
| *G08B 21/06* | (2006.01) | |

(52) U.S. Cl.
CPC .............. *A61B 5/18* (2013.01); *A61B 5/1116* (2013.01); *A61B 5/4806* (2013.01);
(Continued)

(58) Field of Classification Search
CPC .......... A61B 5/168; A61B 5/18; B60W 40/08; B60W 2040/0872
See application file for complete search history.

(56) References Cited

U.S. PATENT DOCUMENTS 6,239,707 B1 5/2001 Park
6,265,978 B1 7/2001 Atlas
(Continued)

FOREIGN PATENT DOCUMENTS

| CN | 101035705 | 9/2007 |
|---|---|---|
| EP | 1 291 226 A2 | 3/2003 |

(Continued)

OTHER PUBLICATIONS

Natasha J., "Introducing a Breakthrough Scout Feature Road Rage Detection BETA", http://blog.scout.me/introducing-a-breakthrough-scout-feature-road-rage-detection-beta/; Apr. 1, 2013, 3 pages.
(Continued)

*Primary Examiner* — Devin B Henson
*Assistant Examiner* — H.Q. Nguyen
(74) *Attorney, Agent, or Firm* — Fish & Richardson P.C.

(57) ABSTRACT

A driver state monitoring (DSM) system includes a wearable device main body worn by a user, a display unit, and an information collection unit that collects information related to a body state of the user. The DSM system includes a controller that, based on the collected information, senses a situation associated with the user's body state, and converts the collected information into a numerical value representing the body state of the user in context of the sensed situation. The controller further calculates a well-driving score for the user based on the numerical value that represents the body state of the user in context of the sensed situation; and controls at least one of the display unit or an image information output device to display the well-driving score and the numerical value that represents the body state of the user in context of the sensed situation.

16 Claims, 12 Drawing Sheets

(52) U.S. Cl.
CPC ............ *A61B 5/4812* (2013.01); *A61B 5/681* (2013.01); *A61B 5/7282* (2013.01); *A61B 5/746* (2013.01); *A61B 5/7435* (2013.01); *G08B 21/06* (2013.01); *A61B 5/1118* (2013.01); *A61B 5/7455* (2013.01); *A61B 5/7475* (2013.01); *A61B 2560/0242* (2013.01)

(56) References Cited

U.S. PATENT DOCUMENTS

| | | |
|---|---|---|
| 2004/0051642 A1 | 3/2004 | Choi |
| 2013/0113910 A1 | 5/2013 | Kim |
| 2013/0226408 A1 | 8/2013 | Fung |
| 2014/0046546 A1 | 2/2014 | Kollegger |

FOREIGN PATENT DOCUMENTS

| | | |
|---|---|---|
| EP | 2 605 228 A2 | 6/2013 |
| KR | 10-2010-0048279 A | 5/2010 |
| KR | 2012-0048981 A | 5/2012 |
| KR | 10-2012-0121074 A | 11/2012 |
| KR | 2013140874 A | 12/2013 |
| WO | 2006037696 | 4/2006 |
| WO | WO 2012/144948 A1 | 10/2012 |

OTHER PUBLICATIONS

European Search Report dated Sep. 29, 2015 for EP Patent Application No. 15001173.2, 7 pages.
European Search Report dated Oct. 19, 2015 for EP Patent Application No. 15001196.3, 5 pages.
Chinese Office Action in Chinese Application No. 201510201453.5, dated Dec. 27, 2016, 19 pages (with English translation).
Chinese Office Action in Chinese Application No. 201510201512.9, dated Dec. 27, 2016, 17 pages (with English translation).
Korean Office Action dated Apr. 1, 2015 for Korean Application No. 10-2014-0068529, 7 Pages.
Korean Notice of Allowance dated Jul. 8, 2015 for Korean Application No. 10-2014-0068529, 2 Pages.

MONITORING A DRIVER OF A VEHICLE

CROSS-REFERENCE TO RELATED APPLICATIONS

This application claims the benefit under 35 U.S.C. § 119(e) of an earlier filing date and right of priority to U.S. Provisional Application No. 61/983,895, filed on Apr. 24, 2014, and the benefit under 35 U.S.C. § 119(a) of an earlier filing date and right of priority to Korean Application No. 10-2014-0068529, filed on Jun. 5, 2014, the contents of which are incorporated by reference herein in their entirety.

TECHNICAL FIELD

This application relates to monitoring a driver of a vehicle.

BACKGROUND

Wearable devices include all various kinds of electronic devices that a user can wear on a user's body or clothes. The wearable devices may be, for example, a smart watch, a wearable computer, Google glasses, a Bluetooth headset, a smart wear, and the like.

Such a wearable device, as described above, is wearable on a user's body or clothes. Accordingly, if the wearable device is used, a various kinds of states related to the user's body can be measured. Currently, studies for enabling advantages of the wearable device to be more widely used are being actively conducted.

SUMMARY

In some aspects, a driver state monitoring (DSM) system is configured to interact with a vehicle. The DSM system includes a wearable device main body configured to be worn by a user, a display unit, and an information collection unit configured to collect information related to a body state of the user. The DSM system also includes a controller. The controller is configured to sense a situation associated with the user's body state based on the collected information and convert the collected information related to the body state of the user into a numerical value that represents the body state of the user in context of the sensed situation, based on pre-stored information for the sensed situation. The controller is also configured to calculate a well-driving score for the user based on the numerical value that represents the body state of the user in context of the sensed situation. The controller is further configured to control at least one of the display unit or an image information output device to display the well-driving score and the numerical value that represents the body state of the user in context of the sensed situation.

In some implementations, the pre-stored information for the sensed situation includes at least one of information obtained by measuring a user's average sleep time, information obtained by measuring a user's average meal size, or information obtained by measuring a user's average exercise quantity. The controller is further configured to determine, based on the sensed situation corresponding to the user sleeping, the user having a meal, or the user exercising, whether the user's sleep state, the user's meal state, or the user's exercise state is excessive or insufficient based on the pre-stored information for the sensed situation, and convert into a numerical value the user's body state for the respective situation based on determining whether the user's sleep state, the user's meal state, or the user's exercise state is excessive or insufficient.

In some implementations, the pre-stored information for the sensed situation further includes information based on a driving behavior of the user corresponding to the body state of the user.

In some implementations, the pre-stored information for the sensed situation further includes at least one of previously collected information regarding an average sleep time, an average meal size, or an average exercise quantity of a person whose age or body information is determined to be relevant to the user The controller is further configured to determine the existence of information obtained by measuring the user's average sleep time, the user's average meal size and the user's average exercise quantity exist; and based on determining the existence of information obtained by measuring the user's average sleep time, the user's average meal size and the user's average exercise quantity exist, convert the user's body state into a numerical value based the previously collected information or based on the measured information.

In some implementations, the controller is further configured to convert the user's body state into a numerical value for the sensed situation further based on a sleeping pattern previously measured for the user.

In some implementations, the controller is further configured to, based on detecting the user's drowsy state, collect information regarding, for each of a plurality of situations, a time from when the situation has ended to when the user's drowsy state is detected. The controller is further configured to determine the user's drowsiness characteristic for each situation by measuring an average duration time for each situation. The controller is further configured to estimate, based on the user's drowsiness characteristic and the time elapsed from when the end of a specific situation is sensed; a time when the user's drowsiness probability is high; and perform at least one predetermined function for preventing the user's drowsy driving at the estimated time. The plurality of situations includes at least one of a situation corresponding to the user having a meal, the user exercising, or the user sleeping.

In some implementations, the function of preventing the user's drowsy driving includes at least one of controlling an audio output unit provided in the vehicle to reproduce a predetermined sound source, providing navigation information on a predetermined specific point through a display unit provided in the vehicle, or controlling a light source of the vehicle.

In some implementations, the function of preventing the user's drowsy driving includes at least one of generating a predetermined vibration pattern, making a call to a predetermined telephone number under a user's selection, or transmitting a message to another person.

In some implementations, the function of preventing the user's drowsy driving includes changing an environmental state of the vehicle to a particular setting among a plurality of settings that are indicated in pre-collected setting information. The pre-collected setting information includes environmental setting information of the vehicle that was collected based on the controller determining that the user was driving the vehicle in an awakened state.

In some implementations, the controller is further configured to determine whether the user's body state is converted into the awakened state subsequent to the environmental state of the vehicle being changed to the particular setting; and, based on determining whether the user's body state is converted into the awakened state subsequent to the environmental state of the vehicle being changed to the particular setting, change the environmental state of the vehicle to another setting or to indicate a weight of the particular setting in the pre-collected setting information.

In some implementations, the controller is further configured to change the environmental state of the vehicle to another setting by selecting a setting from the pre-collected environmental setting information in order of highest weight.

In some implementations, the controller is further configured to display a graphical user interface that enables the user to select, on the display unit, a particular function to be performed for preventing the user's drowsy driving; and enable at least one of the functions for preventing the user's drowsy driving to be performed based on the user's selection.

In some implementations, the controller is further configured to determine whether the user is in a rest state based on a state of the vehicle; and based on determining that the user is in the rest state, change the numerical value corresponding to the user's rest state.

In some implementations, the controller is further configured to determine whether the user's rest state is related to the user's sleep time or the user's exercise quantity, based on at least one of the user's biological information or the user's body posture change information when the driving of the vehicle is stopped; and change at least one of the numerical values related to the user's sleep time or the user's exercise quantity, based on the determined rest state.

In some implementations, the controller is further configured to estimate a user's drowsy driving probability based on the well driving score; and based on the user's drowsy driving probability satisfying a predetermined level, perform at least one of the predetermined functions for preventing the user's drowsy driving.

In some implementations, the controller is further configured to display, on the display unit and based on determining that the driving of the vehicle is ended, a result obtained by measuring a change in the user's body state during driving of the vehicle, and wherein the change in the user's body state is measured based on sensing a biological signal of the user.

In some implementations, the information collection unit is further configured to collect information related to the user's body state from a peripheral device that is external to the DSM system.

In some implementations, the information collection unit is further configured to collect environmental information regarding the vehicle.

In some aspects, a method for controlling a driver state monitoring (DSM) system capable of interacting with a vehicle includes sensing a situation of a user by collecting environmental information around a wearable device worn by the user. The method also includes determining a body state of the user based on the sensed situation and information collected related to the user's body state; and converting the determined body state of the user into a numerical value that represents the body state of the user in context of the sensed situation, based on pre-stored information for the sensed situation associated with the user's body state. The method further includes calculating a well driving score for the user based on the numerical value that represents the body state of the user in context of the sensed situation; and controlling at least one of a display unit or an image information output device to display the numerical value that represents the body state of the user in context of the sensed situation and the well driving score.

In some aspects, a vehicle includes a driver state monitoring (DSM) system. The DSM system is configured to perform operations that include sensing a situation of a user based on environmental information collected around the user and collecting, by a wearable device worn by the user, information related to the user's body state. The operations further include determining the body state of the user based on the sensed situation of the user and the information related to the user's body state; converting the determined body state of the user into a numerical value that represents the body state of the user in context of the sensed situation, based on pre-stored information for the sensed situation; and calculating a well driving score for the user based on the numerical value that represents the body state of the user in context of the sensed situation.

The details of one or more implementations are set forth in the accompanying drawings and the description below. Other features will be apparent from the description and drawings, and from the claims. The description and specific examples below are given by way of illustration only, and various changes and modifications will be apparent.

DETAILED DESCRIPTION

A driver state monitoring (DSM) system is configured to detect and help prevent a user's drowsy driving. The DSM system includes a wearable device that can be worn by the user and interacts with other components of the DSM system. The system analyzes various factors that can cause drowsy driving, including sleeping behavior, eating behavior, and exercise behavior of the user. Based on information that has been collected by the wearable device (e.g., before the user drives, or while the user drives), the DSM system determines whether the user is in a drowsy driving state and performs various functions in response.

For example, in some implementations, the system may utilize information from a past history of the user. For example, in some implementations, the system may utilize cumulative life-log data that has been collected from the wearable device worn by the user. The historical data (e.g., life-log data) of a user may be used to personalize the analysis for the user (e.g., the system may account for a user's high average blood pressure, or low average heart rate, etc.). Based on this historical information of the user, the system may determine a state of the user's body. For example, the system may detect whether the user has gotten enough sleep, eaten enough, has exercised too much, etc. Based on the user's body state, the system may determine the user's ability to safely drive a vehicle. In some implementations, a user's life-log data may be utilized to determine a state of the user's body (e.g., sleepy or awake) and/or the life-log data may be used as a baseline by which other measurements (e.g., measurements taken while the user is driving) may be compared to determine the user's body state.

In some implementations, the system may analyze the data and generate a simple, easy-to-read "well-driving score" (WDS). The system may output the WDS to the user (or other appropriate parties), for example, by displaying the WDS on a user's smart watch (e.g., as a number from 1-100). In some implementations, in addition to displaying a WDS, the system may take other actions (e.g., lock the doors of the vehicle, stop the vehicle, send a message to another person, etc.) based on determining that the user has a high probability of unsafe driving.

Description will now be given in detail according to some implementations disclosed herein, with reference to the accompanying drawings. For the sake of brief description with reference to the drawings, the same or equivalent components may be provided with the same or similar reference numbers, and description thereof will not be repeated. The accompanying drawings are used to help easily understand various technical features and the implementations presented herein are not limited by the accompanying drawings. As such, the present disclosure should be construed to extend to any alterations, equivalents and substitutes in addition to those which are particularly set out in the accompanying drawings.

Figure 1:
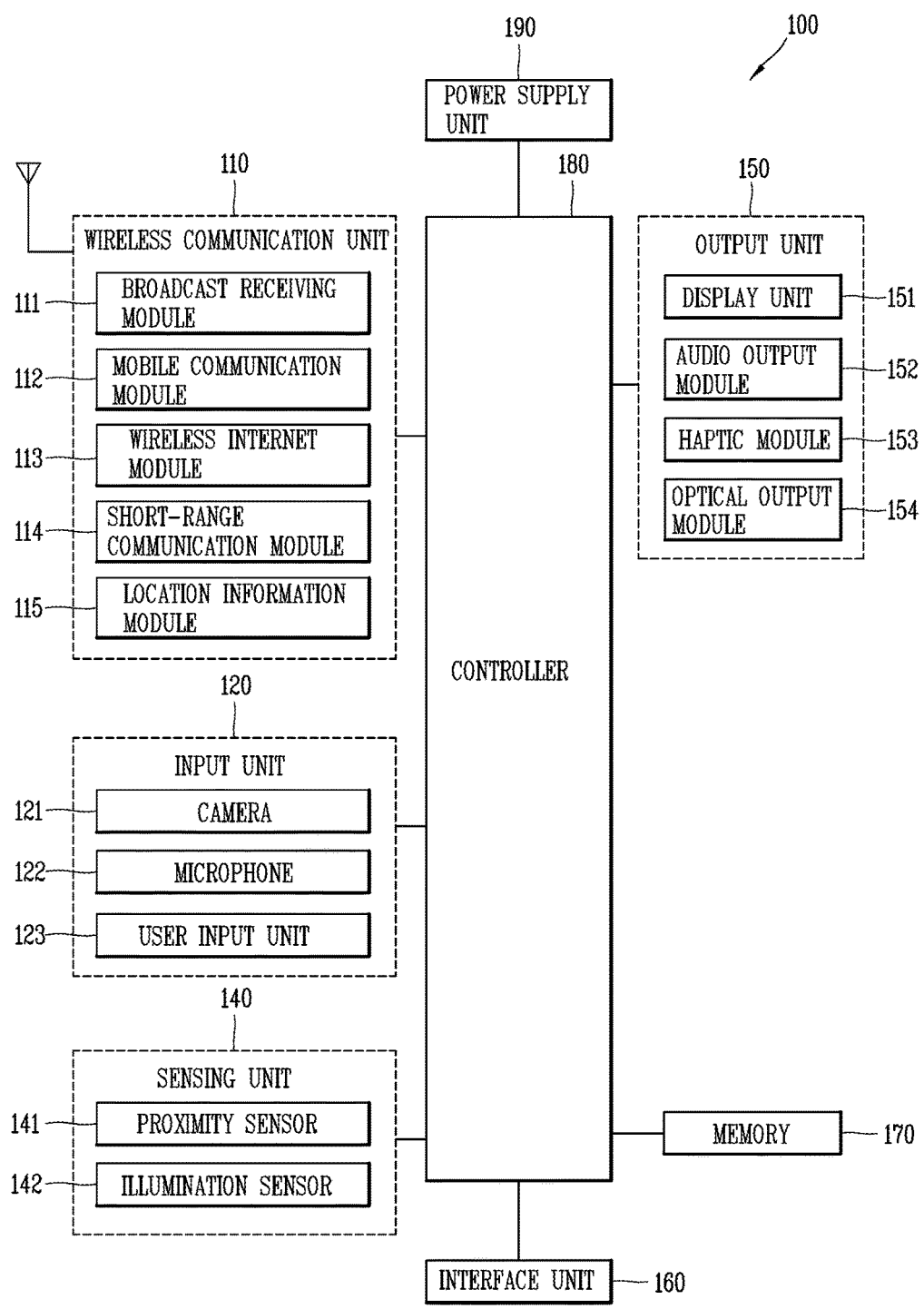
FIG. 1 is a block diagram illustrating an example of a wearable device.

FIG. 1 is a block diagram of an example of a wearable device.

In this example, the wearable device 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

In the example of FIG. 1, the wearable device 100 is shown having wireless communication unit 110 configured with several commonly implemented components. For instance, the wireless communication unit 110 typically includes one or more components which permit wireless communication between the wearable device 100 and a wireless communication system or network within which the wearable device is located.

The wireless communication unit 110 typically includes one or more modules which permit communications such as wireless communications between the wearable device 100 and a wireless communication system, communications between the wearable device 100 and another wearable device, communications between the wearable device 100 and an external server. Further, the wireless communication unit 110 typically includes one or more modules which connect the wearable device 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

In some implementations, the device 100 may include an information collection unit that is configured to collect information regarding a user's physical condition. In some implementations, the information collection unit may include one or more sensors that directly sense the information regarding the user's physical condition. Additionally or alternatively, in some implementations, the information collection unit may include one or more communication units that receive the information regarding the user's physical condition from another device (e.g., an external sensor). Additionally or alternatively, in some implementations, the information collection unit may include one or more input units that receive the information regarding the user's physical condition as direct input from a user.

In the example of FIG. 1, an information collection unit may be implemented, for example, by the wireless communication unit 110 and/or the input unit 120 and/or the sensing unit 140. For example, the sensing unit 140 is typically implemented using one or more sensors configured to sense internal information of the wearable device, the surrounding environment of the wearable device, user information, and the like. For example, in FIG. 1, the sensing unit 140 is shown having a proximity sensor 141 and an illumination sensor 142. If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The wearable device 100 may be configured to utilize information obtained from sensing unit 140, and in particular, information obtained from one or more sensors of the sensing unit 140, and combinations thereof.

In some implementations, the sensing unit 140 may be configured to sense one or more biological signals of a user. For example, the sensing unit may include various sensors (for example, a GSR sensor, a body temperature sensor, a pulse sensor, a pressure sensor, or the like) provided in a body of the wearable device 100.

The biological signal may include various types of information regarding the user (e.g., related to physical activity, sleep, diet, stress, sickness, or other physical conditions or activities) that affect driving ability.

As specific examples, the biological signal may indicate an amount of glucose in the user's blood, which may indicate eating activity by the user. As another example, the biological signal may indicate a heart or pulse rate, indicating sleep or inactivity. As another example, the biological signal may indicate a number of times the user has performed a movement or applied stress to a muscle, which may indicate an exercising movement. Using such examples of biological signals, or others, the sensing unit 140 may collect various types of information that may indicate the user's level of hunger, fatigue, or other physical condition.

The wearable device may also store information related to the user's physical condition, such as the user's age or body weight. Such information may be automatically determined by the wearable device (e.g., based on accessing pre-stored information in other databases) or may be manually entered by the user.

In some implementations, the biological signal refers to an electrical signal generated by the body of the wearer who wears the wearable device 100. For example, the biological signal may be any one of an ECG (ElectroCardioGram) signal, a PPG (Photoplethymogram) signal, and a GSR (Galvanic Skin Response) signal, but the present disclosure is not limited thereto and the biological signal may include any type of signal widely used in the art to measure a sleep stage. For example, a body temperature sensor, a pulse sensor, a pressure sensor, or the like, may additionally or alternatively be included.

As a detailed example, major electrical criteria generated by a body of the wearer may include electro-encephalogram (EEG), electrocardiogram (ECG), an electromyogram (EMG), galvanic skin response, or the like, and major physical criteria includes blood pressure, a heart rate, arrhythmia, a stroke quotient, beat defect, a body temperature, a breathing rate, and the like. At least one or more of the major electrical criteria and major physical criteria may be sensed through sensors provided in the wearable device 100.

In some implementations, an electrocardiogram (ECG) signal is an electrical signal generated from a surface of a skin according to electrical activity of the heart. The ECG signal may be measured by inducing an activity current generated by the heart muscle according to cardiac impulse to two appropriate locations of a body surface.

An electromyogram (EMG) signal is an electrical signal generated from a surface of a skin according to contractile force of muscle, muscle activity, and fatigue of the muscles. EMG may be obtained by sensing a movement of tendons according to a movement of fingers of the wearer sensed when the wearable device 100 is worn. In detail, finger flexor tendons of tendons administering movements of fingers exist in a carpal tunnel within a wrist of the terminal wearer. The finger flexor tendons include nine tendons and one nerve, and when a finger is moved, the nine tendons included in the finger flexor tendons are moved in various combinations. A sensing unit (e.g., the sensing unit 140 in FIG. 1) of the wearable device may sense a shape of the tendons deformed according to a movement of fingers or the wrist, and a controller (e.g., the controller 180 in FIG. 1) may determine which gesture the fingers make based on the sensed information.

The electroencephalogram (EEG) signal is an electrical signal generated from a surface of the skin according to brain activity with respect to concentration or an external stimulus. The EEG signal may be measured by inducing potential fluctuation that occurs in the cerebrum of a person or a brain current generated according to the potential fluctuation from the scalp.

The GSR signal is an electrical signal generated from a surface of the skin according to a change in skin resistance to activity of the sympathetic nerve. The GSR signal may be obtained by measuring a phenomenon that electrical resistance is temporarily reduced, action potential is generated, and the like, due to an external stimulus or emotional excitement in the skin of a living body.

In some implementations, the body sensor periodically detects a temperature of the wrist of the wearer. In this case, when the wearable device 100 is worn on a body part other than on the wrist, a temperature of the body part on which the wearable device 100 is worn is detected. In a case in which the wearable device 100 is worn on a steering wheel of the vehicle, a temperature of the driver's palm holding the steering wheel is periodically detected.

The GSR sensor detects the amplitude of heart beats transmitted through blood and the muscle distributed in the wrist of the wearer and senses a reaction of the body corresponding to a change in an autonomic nerve. Also, in a case in which the wearable device 100 is worn on the steering wheel, for example, a pressure sensor may obtain state information of the driver through a change in pressure (grasping power or grip) of the driver's hand grasping the wheel.

The output unit 150 is typically configured to output various types of information, such as audio, video, tactile output, and the like. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the wearable device 100 and a user, as well as function as the user input unit 123 which provides an input interface between the wearable device 100 and the user.

The interface unit 160 serves as an interface with various types of external devices that can be coupled to the wearable device 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the wearable device 100 may perform assorted control functions associated with a connected external device, in response to the external device being connected to the interface unit 160.

The memory 170 is typically implemented to store data to support various functions or features of the wearable device 100. For instance, the memory 170 may be configured to store application programs executed in the wearable device 100, data or instructions for operations of the wearable device 100, and the like. Some of these application programs may be downloaded from an external server via wireless communication. Other application programs may be installed within the wearable device 100 at time of manufacturing or shipping, which is typically the case for basic functions of the wearable device 100 (for example, receiving a call, placing a call, receiving a message, sending a message, and the like). It is common for application programs to be stored in the memory 170, installed in the wearable device 100, and executed by the controller 180 to perform an operation (or function) for the wearable device 100.

The controller 180 typically functions to control overall operation of the wearable device 100, in addition to the operations associated with the application programs. The controller 180 may provide or process information or functions appropriate for a user by processing signals, data, information and the like, which are input or output by the various components depicted in FIG. 1, or activating application programs stored in the memory 170.

As one example, the controller 180 controls some or all of the components illustrated in FIG. 1 according to the execution of an application program that have been stored in the memory 170. For driving of the application program, the controller 180 may operate the wearable device 100 by combining at least two of the components of the wearable device 100.

The power supply unit 190 can be configured to receive external power or provide internal power in order to supply appropriate power required for operating elements and components included in the wearable device 100. The power supply unit 190 may include a battery, and the battery may be configured to be embedded in the terminal body, or configured to be detachable from the terminal body.

At least part of the components may operate in a cooperating manner, so as to implement an operation, a control, or a control method of a wearable device according to various implementations. The operation, the control, or the control method of the wearable device may be implemented on the wearable device, by driving of at least one application program stored in the memory 170

Referring to FIG. 1, various components depicted in this figure will now be described in more detail. Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some implementations, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external wearable device, a server, and the like. Such network entities form part of a mobile communication network, which is constructed according to technical standards or communication methods for mobile communications (for example, Global System for Mobile Communication (GSM), Code Division Multi Access (CDMA), CDMA2000(Code Division Multi Access 2000), EV-DO(Enhanced Voice-Data Optimized or Enhanced Voice-Data Only), Wideband CDMA (WCDMA), High Speed Downlink Packet access (HSDPA), HSUPA(High Speed Uplink Packet Access), Long Term Evolution (LTE), LTE-A(Long Term Evolution-Advanced), and the like). Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the wearable device 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA(High Speed Uplink Packet Access), Long Term Evolution (LTE), LTE-A(Long Term Evolution-Advanced), and the like. The wireless Internet module 113 may transmit/receive data according to one or more of such wireless Internet technologies, and other Internet technologies as well.

In some implementations, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the wearable device 100 and a wireless communication system, communications between the wearable device 100 and another wearable device 100, or communications between the wearable device and a network where another wearable device 100 (or an external server) is located, via wireless area networks. One example of the wireless area networks is a wireless personal area networks.

In some implementations, another wearable device (which may be configured similarly to wearable device 100) may be a wearable device, for example, a smart watch, a smart glass or a head mounted display (HMD), which is able to exchange data with the wearable device 100 (or otherwise cooperate with the wearable device 100). The short-range communication module 114 may sense or recognize the wearable device, and permit communication between the wearable device and the wearable device 100. In addition, when the sensed wearable device is a device which is authenticated to communicate with the wearable device 100, the controller 180, for example, may cause transmission of data processed in the wearable device 100 to the wearable device via the short-range communication module 114. Hence, a user of the wearable device may use the data processed in the wearable device 100 on the wearable device. For example, when a call is received in the wearable device 100, the user may answer the call using the wearable device. Also, when a message is received in the wearable device 100, the user can check the received message using the wearable device.

The location information module 115 is generally configured to detect, calculate, derive or otherwise identify a position of the wearable device. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the wearable device.

As one example, when the wearable device uses a GPS module, a position of the wearable device may be acquired using a signal sent from a GPS satellite. As another example, when the wearable device uses the Wi-Fi module, a position of the wearable device can be acquired based on information related to a wireless access point (AP) which transmits or receives a wireless signal to or from the Wi-Fi module.

The input unit 120 may be configured to permit various types of input to the wearable device 100. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the wearable device 100. As another example, the cameras 121 may be located in a stereoscopic arrangement to acquire left and right images for implementing a stereoscopic image.

The microphone 122 is generally implemented to permit audio input to the wearable device 100. The audio input can be processed in various manners according to a function being executed in the wearable device 100. If desired, the microphone 122 may include assorted noise removing algorithms to remove unwanted noise generated in the course of receiving the external audio.

The user input unit 123 is a component that permits input by a user. Such user input may enable the controller 180 to control operation of the wearable device 100. The user input unit 123 may include one or more of a mechanical input element (for example, a key, a button located on a front and/or rear surface or a side surface of the wearable device 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the wearable device at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the wearable device, surrounding environment information of the wearable device, user information, or the like. The controller 180 generally cooperates with the sending unit 140 to control operation of the wearable device 100 or execute data processing, a function or an operation associated with an application program installed in the wearable device based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the wearable device covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and cause output of visual information on the touch screen. In addition, the controller 180 can control the wearable device 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

In some implementations, the controller 180 may execute the same or different controls according to a type of touch object that touches the touch screen or a touch key provided in addition to the touch screen. Whether to execute the same or different control according to the object which provides a touch input may be decided based on a current operating state of the wearable device 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the wearable device 100. For example, the display unit 151 may display execution screen information of an application program executing at the wearable device 100 or user interface (UI) and graphic user interface (GUI) information in response to the execution screen information.

In some implementations, the display unit 151 may be implemented as a stereoscopic display unit for displaying stereoscopic images.

A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the wearable device 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the wearable device 100.

An optical output module 154 can output a signal for indicating an event generation using light of a light source. Examples of events generated in the wearable device 100 may include message reception, call signal reception, a missed call, an alarm, a schedule notice, an email reception, information reception through an application, and the like.

A signal output by the optical output module 154 may be implemented in such a manner that the wearable device emits monochromatic light or light with a plurality of colors. The signal output may be terminated as the wearable device senses that a user has checked the generated event, for example.

The interface unit 160 serves as an interface for external devices to be connected with the wearable device 100. For example, the interface unit 160 can receive data transmitted from an external device, receive power to transfer to elements and components within the wearable device 100, or transmit internal data of the wearable device 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various types of information for authenticating authority of using the wearable device 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the wearable device 100 is connected with an external cradle, the interface unit 160 can serve as a passage to allow power from the cradle to be supplied to the wearable device 100 or may serve as a passage to allow various command signals input by the user from the cradle to be transferred to the wearable device there through. Various command signals or power input from the cradle may operate as signals for recognizing that the wearable device is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The wearable device 100 may also be operated in relation to a network storage device that performs the storage function of the memory 170 over a network, such as the Internet.

The controller 180 may typically control the general operations of the wearable device 100. For example, the controller 180 may set or release a lock state for restricting a user from inputting a control command with respect to applications when a status of the wearable device meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various some implementations disclosed herein.

The power supply unit 190 receives external power or provide internal power and supply the appropriate power required for operating respective elements and components included in the wearable device 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various implementations described herein may be implemented in a computer-readable medium, a machine-readable medium, or similar medium using, for example, software, hardware, or any combination thereof.

In some implementations, a wearable device 100 may be configured as a device which is wearable on a human body. Examples of the wearable device 100 include a smart watch, a smart glass, a head mounted display (HMD), and the like. In some implementations, the wearable device 100 may cooperate with another device (e.g., another wearable device, a smart phone, etc.).

As a specific example, the wearable device 100 can exchange data with (or cooperate with) another mobile device (e.g., another wearable device or a smart phone, etc.). In such a scenario, the wearable device 100 may have functionality that is less than the cooperating mobile device. For instance, the short-range communication module 114 of the wearable device 100 may sense or recognize a wearable device that is near-enough to communicate with the cooperating mobile device. In addition, when the sensed mobile device is a device which is authenticated to communicate with the wearable device 100, the controller 180 may transmit data processed in the wearable device 100 to the mobile device via the short-range communication module 114 (or the wearable device 100 may receive data that was processed in the cooperating mobile device), for example. Hence, a user of the cooperating mobile device can use the data processed in the wearable device 100 on the mobile device, or can use data processed in the mobile device on the wearable device 100. For example, when a call is received on the cooperating mobile device (e.g. a smart phone), the user can answer the call using the wearable device 100. As another example, when a message is received on the cooperating mobile device (e.g., a smart phone), the user can check the received message using the wearable device 100.

Figure 2:
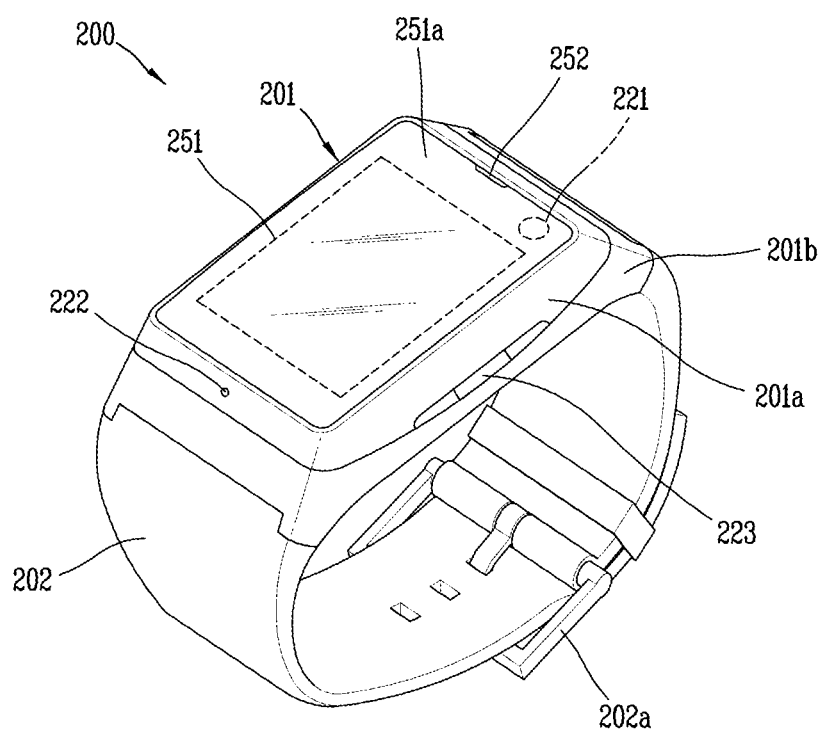
FIG. 2 is a perspective view illustrating an example of a watch-type wearable device.

FIG. 2 is a perspective view illustrating an example of a watch-type wearable device. As illustrated in FIG. 2, the watch-type wearable device 200 includes a main body 201 with a display unit 251 and a band 202 connected to the main body 201 to be wearable on a wrist. In general, wearable device 200 may be configured to include features that are the same or similar to that of wearable device 100 of FIG. 1.

The main body 201 may include a case having a certain appearance. As illustrated, the case may include a first case 201a and a second case 201b cooperatively defining an inner space for accommodating various electronic components. Other configurations are possible. For instance, a single case may alternatively be implemented, with such a case being configured to define the inner space, thereby implementing a wearable device 200 with a uni-body.

The watch-type wearable device 200 can perform wireless communication, and an antenna for the wireless communication can be installed in the main body 201. The antenna may extend its function using the case. For example, a case including a conductive material may be electrically connected to the antenna to extend a ground area or a radiation area.

The display unit 251 is shown located at the front side of the main body 201 so that displayed information is viewable to a user. In some implementations, the display unit 251 includes a touch sensor so that the display unit can function as a touch screen. As illustrated, window 251a is positioned on the first case 201a to form a front surface of the terminal body together with the first case 201a.

The illustrated example includes audio output module 252, a camera 221, a microphone 222, and a user input unit 223 positioned on the main body 201. When the display unit 251 is implemented as a touch screen, additional function keys may be minimized or eliminated. For example, when the touch screen is implemented, the user input unit 223 may be omitted.

The band 202 is commonly worn on the user's wrist and may be made of a flexible material for facilitating wearing of the device. As one example, the band 202 may be made of fur, rubber, silicon, synthetic resin, or the like. The band 202 may also be configured to be detachable from the main body 201. Accordingly, the band 202 may be replaceable with various types of bands according to a user's preference.

In one configuration, the band 202 may be used for extending the performance of the antenna. For example, the band may include therein a ground extending portion (not shown) electrically connected to the antenna to extend a ground area.

The band 202 may include fastener 202a. The fastener 202a may be implemented into a buckle type, a snap-fit hook structure, a Velcro® type, or the like, and include a flexible section or material. The drawing illustrates an example that the fastener 202a is implemented using a buckle.

In some implementations, the watch-type device 200 may include one or more sensors for sensing whether a user is drowsy. For example, the watch-type device 200 may include a sensing unit (e.g., sensing unit 140 in FIG. 1) that includes one or more sensors that detect one or more biological signals of a user. Such sensors may be included on any suitable portion of the watch-type device 200, such as on the main body 201, band 202, or other part of the watch-type device 200. In some implementations, the sensing unit (e.g., sensing unit 140 in FIG. 1), or one or more sensors of the sensing unit, may be physically separate from the main body of the watch-type device 200 and may be communicative (e.g., via wireless communication) with the controller (e.g., controller 180 in FIG. 1) of the watch-type device 200. For example, in some implementations, sensors may include a camera that is remote from the watch-type device 200 (e.g., installed in the vehicle) and communicative with the watch-type device 200 to provide image information regarding the user who wears the watch-type device 200.

Figure 3:
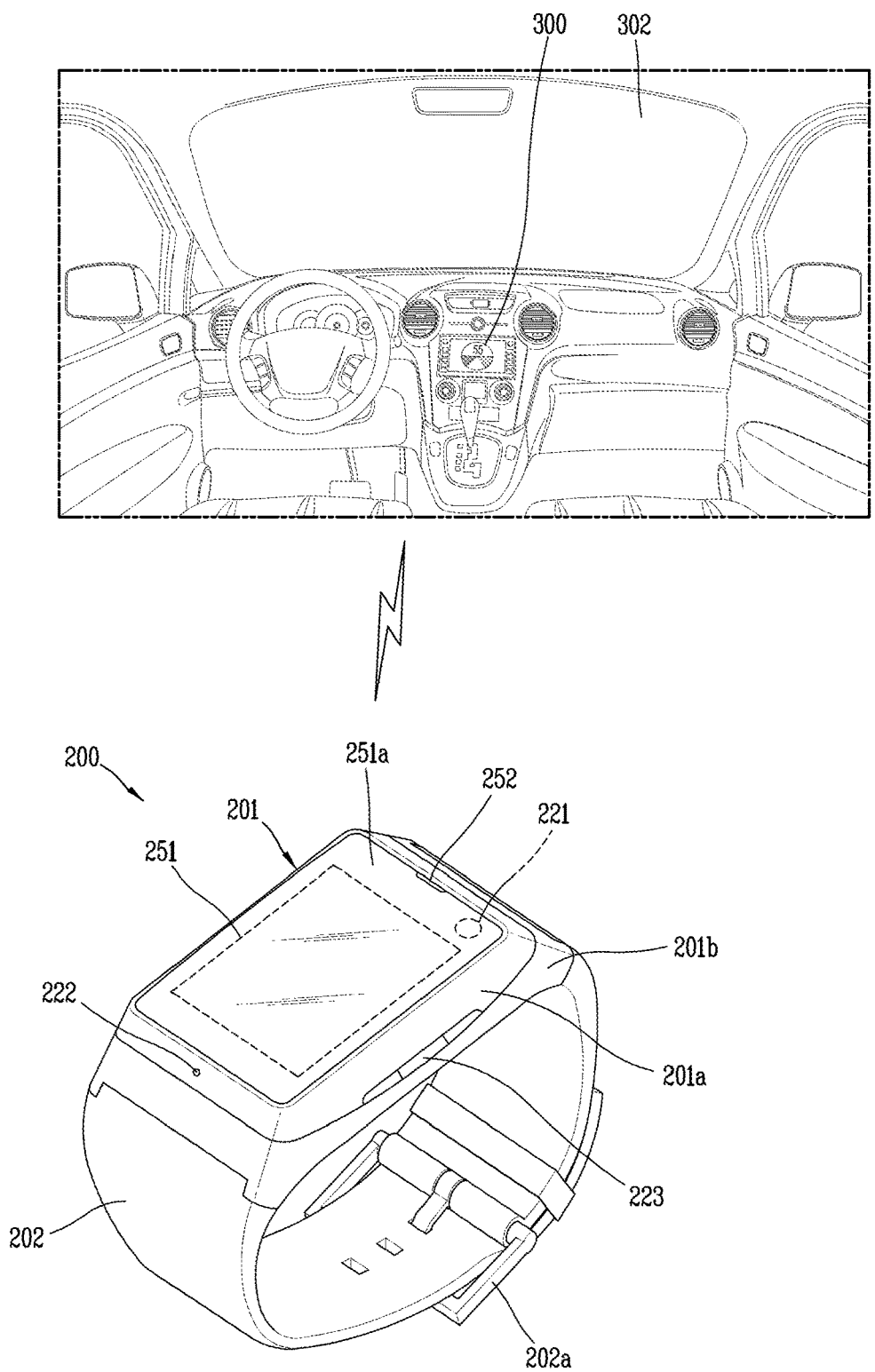
FIG. 3 is sketch illustrating an example of a smart watch operating in conjunction with a vehicle.

FIG. 3 is sketch illustrating an example in which a smart watch interacts with a vehicle.

In the example of FIG. 3, the wearable device 200 may be connected by wire or wireless to a controller (not shown) of a vehicle to request the controller to perform a specific function. The state in which the vehicle interacts with the wearable device 200 by being connected to the wearable device 200 as described above is referred to as a 'connected car' state.

If the state becomes the 'connected car' state as described above, the wearable device 200 may transmit image information and/or sound information output from the wearable device 200 through a predetermined interface to an audio/video (NV) output device provided in the vehicle. The image information and/or sound information transmitted to the output device of the vehicle as described above may be output through a display unit 300 and/or an audio system (not shown), provided in the vehicle. In this state, the interface for transmitting the image information and/or sound information, for example, may be a means for supporting wireless communication, such as a wireless fidelity (WiFi) transceiver or Bluetooth transceiver, or a means for supporting wire communication, such as a universal serial bus (USB) terminal.

In some implementations, if the state becomes the 'connected car' state, the wearable device 200 may allow at least one of executable functions in the vehicle to be performed. For example, the wearable device 200 may allow image information output in the display unit 251 to be displayed in a head up display (HUD) scheme through the display unit 300 provided in the vehicle or a wind shield glass 302 of the vehicle. Alternatively or additionally, the wearable device 200 may suggest that a user open the window of the vehicle or reproduce specific music data through an interface displayed on the display unit 251 thereof. Alternatively or additionally, the wearable device 200 may allow navigation information related to a predetermined specific point to be displayed on the display unit 300 of the vehicle.

If the state becomes the 'connected car' state, the controller (not shown) of the vehicle may obtain an image of a driver through a camera provided in the vehicle, e.g., a camera mounted inside the vehicle, and transmit the obtained image to the wearable device 200 connected to the vehicle. Then, the wearable device 200 may analyze the obtained image and detect a state in which the driver's head moves and/or a number of times or time when the driver closes eyes. In addition, the wearable device 200 may decide whether the driver is drowsy during driving of the vehicle, using the analyzed image.

Hereinafter, some implementations related to a control method implemented in the wearable device configured as described above will be described with reference to the accompanying drawings. In the following description, the case where a smart watch is used as an example of the wearable device 200 will be described for convenience. However, implementations are not limited thereto.

Figure 4:
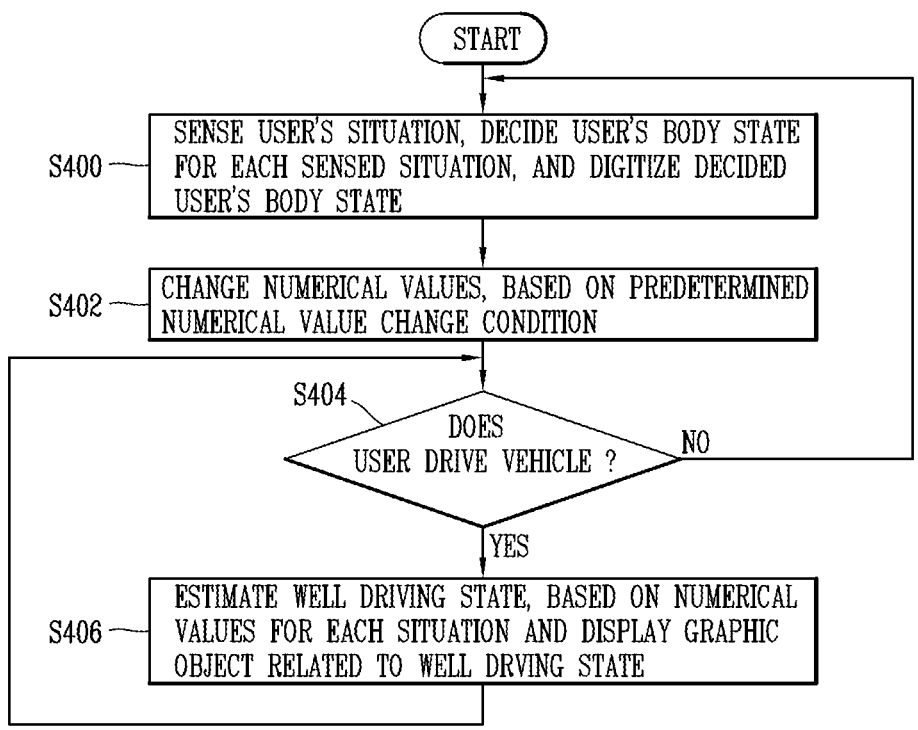
FIG. 4 is a flowchart illustrating an example of an operation process of a smart watch.

FIG. 4 is a flowchart illustrating an example of an operation process of a smart watch in a DSM system.

Referring to FIG. 4, the controller 180 of the smart watch 100 according to some implementations senses a user's situations, decides a user's body state for each of the sensed user's situations, and converts the decided user's body state into numerical values (e.g., by digitizing the user's body state), based on predetermined information (S400).

In step S400, the controller 180 may sense a user's current situation, using various sensors provided in the sensing unit 140. For example, the controller 180 may sense a state in which the user is exercising, based on measurement values of an inertia sensor, a gyro sensor and the like, provided in the sensing unit 140, and a result obtained by sensing a user's heart rate or body temperature. Alternatively or additionally, the controller 180 may sense that the user is currently having a meal, based on an increment of glucose in blood or information on the current position of the smart watch 100. Alternatively or additionally, the controller 180 may sense whether the user is in a sleep state, based on a sensing value of the illumination sensor 142 or a result obtained by sensing an environment around the smart watch 100.

Based on various situations that are sensed as described above, the controller 180 determines a user's body state for each of the sensed situations. For example, based on determining that sensed situation corresponds to the user currently having a meal, the controller 180 may determine whether the user is in a state of overeating. As another example, based on determining that the sensed situation corresponds to the user exercising, the controller 180 may determine whether the user's body state is excessively exercising. As another example, based on determining that the sensed situation corresponds to the user sleeping, the controller 180 may decide whether the user's body is in a sleep deprivation state (e.g., by measuring the user's sleep time).

There may be several methods by which the controller may determine the user's body state. For example, the controller 180 may determine whether the user overeats based on user's biological information such as an amount of glucose in user's blood or a number of times of moving an arm on which the smart watch 100 is worn at a predetermined level or more. The controller 180 may determine whether the user is excessively exercising based on an exercise quantity measured using the user's biological information or the user's age or body weight. When the user is in the sleep state, the controller 180 may measure a user's sleep time through various methods and determine whether the user is in the sleep deprivation state, based on the measured sleep time.

In some implementations, in step S400, the controller 180 differently digitizes the user's body states for the respective sensed situations. For example, when the sensed user's situation is a situation of 'meal', the controller 180 may digitize the decided user's body states, i.e., an overeating state, a light eating state and an appropriate state into different values. When the sensed user's situation is a situation of 'exercise', the controller 180 may digitize an excessive exercise state, an exercise deprivation state and an appropriate state into different values. When the sensed user's situation is a situation of 'sleep', the controller 180 may decide a user's body state as an excessive sleep state, a sleep deprivation state or an appropriate sleep state, based on the measured user's sleep time, and digitize the decided user's body state, using corresponding values. Here, the corresponding values may be values previously determined by experiments to respectively correspond to various user's body states.

In some implementations, the numerical value determined based on a user's body state for each situation may be a numerical value related to user's well driving. For example, the 'well driving' may mean a time or state where the user can safely drive the vehicle without falling asleep. In some implementations, the 'numerical value related to the well driving' may be a numerical value for estimating a 'well driving' state, based on the decided user's body state. As an example, if the numerical value is high, the 'well driving' may correspond to a state in which the 'well driving' is possible for a longer period of time. If the numerical value is low, the 'well driving' may correspond to a state in which the 'well driving' is possible for a shorter period of time.

In some implementations, in step S400, based on the user's body state determined for each of the sensed situations being converted into a numerical vale related to well driving, the controller 180 determines whether a predetermined numerical value change condition for each situation occurs, and changes the numerical values (numerical values related to the well driving), based on the decided result (S402).

In step S402, the numerical values related to the well driving may be changed depending on a predetermined change condition. For example, the numerical values may be gradually decreased according to time (e.g., reflecting the fatigue accumulated in user's daily life). Alternatively, the numerical values decided in step S400 may be renewed due to the occurrence of an identical or similar situation (e.g., when the user exercises again in the afternoon after the exercise in the morning, or when the user has lunch or dinner after the breakfast).

In some implementations, in step S402, the controller 180 may allow the numerical values to be changed based on a user's drowsiness characteristic previously detected for each situation. For example, the controller 180 may detect a situation in which the user is more drowsy than usual or a situation in which the user is less drowsy than usual, based on the result obtained by sensing a state in which the user is drowsy. The controller 180 may allow the numerical value related to the well driving, corresponding to a specific situation, to be more quickly or more slowly decreased according to the user's drowsiness characteristic.

The controller 180 determines whether the user's state is a state in which the user drives the vehicle (S404). For example, when the smart watch 100 moves to the interior of the vehicle, and the user is predetermined as the driver of the vehicle (e.g., based on the position of a seat taken by the user corresponding to the driver's seat), the controller 180 may determine that the user has driven the vehicle when a movement of the vehicle is detected at a predetermined speed or for more than a predetermined time.

Based on determining in step 404 that the user has driven the vehicle, the controller 180 may estimate a user's well driving state according to a well driving score (WDS) calculated based on the numerical values related to well driving. In addition, the controller 180 may display (e.g., in the display unit 151) a graphic object related to the user's well driving state (S406). The graphic object may be displayed, for example, in the HUD scheme through the display unit 300 provided in the vehicle or the wind shield glass of the vehicle, as well as the display unit 151 formed in the smart watch 100.

In some implementations, the controller 180 may use, as the WDS, a result obtained by adding up the numerical values related to the well driving for the respective situations. In this case, the WDS may represent a user's current well driving state. As the WDS becomes high, the user's well driving state may be maintained for a long period of time.

In some implementations, when the graphic object related to the well driving state is displayed, the controller 180 may display the graphic object so that the user can recognize each numerical value related to the well driving. In this state, the weight that the numerical values related to the well driving occupy in the WDS is displayed to the user so that the user can take an action for maintaining the WDS.

For example, if the numerical values related to the well driving are ones related to the user's sleep, meal or exercise state, the user may identify the numerical values related to the well driving, respectively corresponding to the sleep, meal and exercise states, through the graphic object, and recognize the numerical value related to the well driving, which currently shows the lowest numerical value. In this case, if the numerical value related to the well driving, which currently shows the lowest numerical value, is related to the user's sleep state, the user may take an action for increasing the numerical value related to the user's sleep state (e.g., stopping driving of the vehicle and having a sleep for a certain period of time). The controller 180 may sense a change in the user's state so that the numerical value related to the sensed change is increased, and accordingly, the WDS can be further increased.

In some implementations, in step S406, the numerical values related to the well driving may gradually decrease based on the time for which the user drives the vehicle. Here, the controller 180 may allow a user's predetermined drowsiness characteristic (e.g., a sleeping pattern based on a life-log history) to be reflected in changing of the numerical values related to the well driving. For example, in case of a numerical value related to the well driving, where the user who takes excessive exercise is more drowsy than usual, the controller 180 may allow the numerical value related to the excessive exercise among the numerical values related to the well driving to be more quickly decreased. Alternatively, in case of a numerical value related to the well driving, where the user is less drowsy than usual, the controller 180 may allow the numerical value related to the well driving to be more slowly decreased.

The decreased numerical values related to the well driving may be again increased based on a predetermined condition. For example, when the user stops the driving of the vehicle and takes a rest, the controller 180 may increase the numerical values related to the well driving, based on the predetermined condition. For example, when the user identifies a WDS and numerical values related thereto, displayed on the display unit 151, and stops the driving of the vehicle and then has a sleep for a while, the controller 180 may sense a state in which the user has a sleep, and allow the numerical value related to the user's sleep state among the numerical values related to the well driving to be increased. In some implementations, the controller 180 may decide the state in which the user has a sleep, based on user's biological information, etc., sensed through the sensing unit 140.

In some implementations, one or more of the foregoing processes (e.g., steps S404 and S406) may be repeatedly performed while the user is driving the vehicle. When the user ends the driving of the vehicle, i.e., when the user does not drive the vehicle, the controller 180 again proceeds to step S400 to sense a user's situation and convert the user's body state into a numerical value based on the sensed situation. In some implementations, the controller 180 may repeatedly perform step S400 and step 402 in which the numerical values are renewed during the time when the user does not drive the vehicle. Thus, in some implementations, a database including a user's lifestyle and various information related to the user's lifestyle can be generated based on data accumulated by sensing a user's body state for each situation and measuring the sensed user's state. In addition, the database can be used as data for deciding the user's drowsiness characteristic and user's characteristics.

Although the foregoing description has focused on situations in which the user has a meal, the user exercises, and the user sleeps, these are only some examples of possible situations that the system may sense, and other implementations are possible in which other types of situations of the user are sensed. Thus, the system may sense various different situations of the user and convert the user's body state for each corresponding situation into a numerical value related to the well driving.

In some implementations, the controller 180 does not sense a situation but may directly receive information on a specific situation, input from the user. For example, the controller 180 may recognize whether the user is currently having a meal, exercising or sleeping, based on the information input from the user. Alternatively, the controller 180 may recognize whether the user overeats or eats little, or how long the user sleeps, based on the information directly input from the user.

The controller 180 may reflect a numerical value input directly by the user regarding the well driving. For example, the user may input a stress index measured through a means capable of measuring stress, an item related to when the user is on night duty, or the like. In this case, the controller 180 may allow the numerical values related to the well driving to be changed by reflecting the item input by the user. That is, the controller 180 may allow the speed at which the numerical value related to the well driving decreases to become faster, for example, when the user is on night duty or when the user's stress index is high.

In some implementations, in step S406, the controller 180 may decide a user's drowsy driving possibility, based on the WDS. As described above, the 'well driving' can correspond to a time or state where the user can safely drive the vehicle without falling asleep. In some implementations, when the WDS representing the 'well driving' state is a predetermined level or less, the controller 180 may decide that the user cannot maintain the well driving, i.e., that the user's drowsy driving possibility is high.

In some implementations, the controller 180 can decide the user's drowsy driving probability, based on the WDS. In some implementations, the controller 180 may enable a predetermined drowsy driving prevention function to be performed based on the WDS.

For example, the function may be a function of reproducing a predetermined sound source or changing various environmental states of the vehicle such as changing an illumination (light source) inside the vehicle or controlling an open/close state of window. Alternatively or additionally, the function may be a function of making a call to a predetermined telephone number. Alternatively or additionally, the function may be a function of providing navigation information on a predetermined specific point. Hereinafter, an example of the function will be described in detail with reference to FIG. 8 which illustrates details of an example of the operation of step S406.

The function may be provided in the form of inviting or proposing the user so that the user can select whether the function is provided. The controller 180 may allow different functions to be selected based on the estimated user's drowsy driving possibility.

As such, in some implementations, the user's well driving state, i.e., the state in which the user can drive the vehicle without falling asleep is digitized and visually displayed. Accordingly, the user can intuitively recognize a driving possibility degree, based on a user's current body state. Further, the numerical value related to a user's body state for each situation is displayed, so that the user can take an action required to maintain the well driving state.

Although examples have been described in which the user's drowsy driving probability is estimated based on the WDS, in some implementations the user's drowsy driving possibility may be estimated by further considering the user's drowsiness characteristic as well as the WDS.

For example, the controller 180 may allow the numerical values related to the well driving to be more quickly decreased based on the user's drowsiness characteristic related to a driving time of the vehicle. Alternatively or additionally, when the user has a drowsiness characteristic that the user is frequently drowsy during driving of the vehicle in a specific situation, e.g., a state such as an overeat state, the controller 180 may previously estimate a time when the user is frequently drowsy, based on the drowsiness characteristic. The controller 180 may allow at least one function of preventing the user's drowsy driving at the estimated time.

Figure 5:
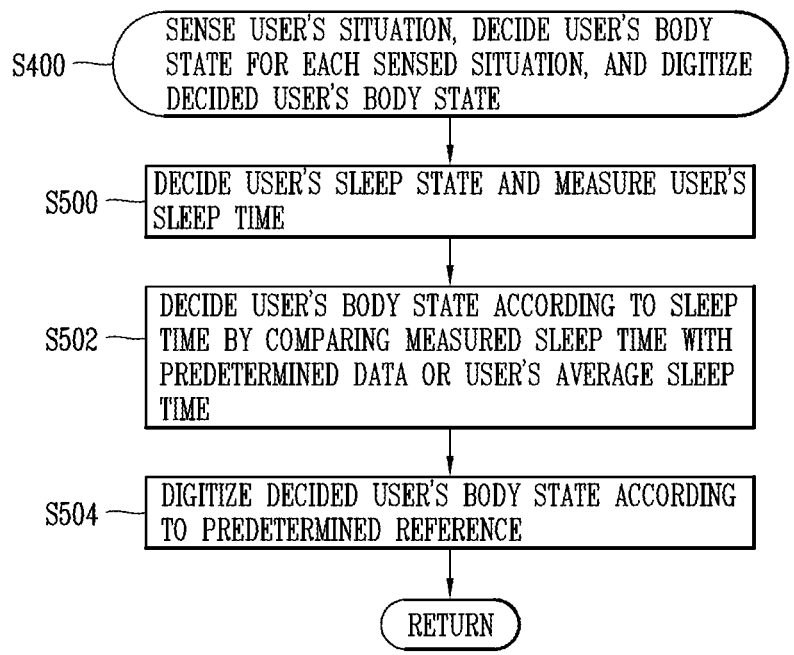
FIG. 5 is a flowchart illustrating an example of using a smart watch to sense a user's body state and digitize the sensed user's body state.

In some implementations, as described above, the controller 180 of the smart watch 100 may sense a user's various situations including when the user sleeps, when the user has a meal, when the user exercises, and the like, and decide a user's body state for each situation. In this case, the method in which the controller 180 senses the user's situation may be varied. FIG. 5 is a flowchart illustrating an example of an operation process of sensing a user's body state and digitizing the sensed user's body state, when the user has a sleep, in a smart watch of a DSM system.

Referring to FIG. 5, when the user is sleeping, the controller 180 may sense the user's sleep and check a user's sleep time (S500). For example, the controller 180 may decide whether the user is in a sleep state, based on a user's biological signal, i.e., a user's pulse, body temperature or breathing rate. Alternatively or additionally, when the illumination intensity sensed by the illumination sensor 142 is a predetermined level or less, the controller 180 may decide that the user is in the sleep state. Alternatively or additionally, the controller 180 may use connectable peripheral devices to sense the user's sleep state. Here, the connectable peripheral devices may be home electronic devices such as an electric lamp and a TV, installed in the user's home.

In some implementations, even when no biological signal is obtained from the user (e.g., when the user does not wear the smart watch 100), the controller 180 may use information obtained from a home electronic device such as an electric lamp or TV. For example, when both the electric lamp and the TV are turned off, the controller 180 may decide that the user is in the sleep state. Alternatively or additionally, when biological information can be obtained for sensing the user's sleep state (e.g., via the TV), the controller 180 may sense that the user is in the sleep state by receiving the obtained information.

The controller 180 may measure a user's sleep time. For example, the controller 180 may sense that the user has woken up, based on the sensed intensity, the case where the TV or electric lamp is turned on, or the result obtained by sensing an ambient noise or motion. In this case, the controller 180 may measure, as the user's sleep time, a time from when the user enters into the sleep state to when the user wakes up.

If the user's sleep time is measured as described above, the controller 180 may decide whether the user is in a sleep deprivation state, based on the measured sleep time. For example, the controller 180 may decide whether the measured user's sleep time is sufficient or insufficient, based on a general statistical value (S502). Here, the general statistical value may be previously stored one or one downloaded from an exterior (e.g., a cloud server).

Alternatively or additionally, the controller 180 may use data obtained by measuring a user's average sleep time in order to decide whether the measured sleep time is insufficient. That is, the controller 180 may measure the user's average sleep time, based on the user's sleep time measured in step S500, and decide whether the user's sleep time is currently sufficient or insufficient based on the measured average sleep time.

In some implementations, the decision of whether the user's sleep time is insufficient based on the user's average sleep time may be more accurate than the decision of whether the user's sleep time is insufficient based on statistical values. Therefore, in some implementations, in the decision of whether the user's sleep time is insufficient, the controller 180 may first use the user's average sleep time, and may use the general statistical value only when there is no data obtained by measuring the user's average sleep time or when it is insufficient to calculate the user's average sleep time.

In some implementations, if a user's body state (a sleep deprivation state, or the like) is decided in step S502, the controller 180 may convert the decided user's body state into a numerical value that is related to the well driving (S504). Here, the numerical value related to the well driving may be a value previously determined by experiments using different values according to the decided user's body state, i.e., a sleep deprivation state or excessive sleep state, or the time taken for the user to sleep. In addition or as an alternative, the decided user's body state may be represented in relation to the well driving. That is, when the user's sleep time is insufficient, the numerical value corresponding to the insufficient sleep time may have a low value. In some implementations, when the user's sleep time is sufficient, the numerical value corresponding to the sufficient sleep time may have a high value. For example, as the user sufficiently sleeps, the system may determine that well driving is possible for a longer period of time.

Based on determining that the user has been sleeping, as described above, the controller 180 may sense the user's sleep state and convert a user's body state into a numerical value that is related to the well driving. In the example described above, although the case where the user has a sleep has described as an example, the user's body state may be converted into a numerical value related to the well driving even in other situations as well, e.g., when the user has a meal or when the user takes exercise.

As an example, when the user has a meal, the controller 180 may sense the user's meal state. For example, the controller 180 may sense when the user enters into a dining room, using a result obtained by sensing movement of the position of the smart watch 100 or a sensor inside the dining room. When the user stays inside the dining room for a certain period of time, the controller 180 may decide that the user has a meal. Alternatively or additionally, when a material or tableware related to food is moved as a result obtained by sensing ambient sounds or when a sound generated when the user eats food (e.g., a chewing sound) is sensed, the controller 180 may sense a situation in which the user has a meal. Alternatively or additionally, the controller 180 may sense a state in which the user has a meal, based on biological information obtained from the user (e.g., an amount of glucose in blood, an increase in body temperature or heart rate corresponding to a digestion state, or the like).

The controller 180 may decide a user's body state corresponding to the sensed situation. For example, the controller 180 may decide the user's meal size, based on at least one of an amount of glucose in user's blood, a time when the increase in the body temperature or heart rate corresponding to the digestion state is maintained, and at a time when the user stays in the dining room. In addition, the controller 180 may decide whether the user overeats based on the decided meal size and a pre-stored information.

Here, the pre-stored information, as similarly to that shown in FIG. 5, may be information related to a general statistical value or a user's average meal size. That is, the controller 180 may previously store information on an average meal size of people similar to the user, based on the user's age, weight and sex, and decide whether the user overeats based on the stored information and the measured meal size.

Alternatively, the pre-stored information may be one on the user's average meal size. For example, the controller 180 may obtain the information on the user's average meal size by collecting information on the user's meal sizes and calculating an average of the information. The controller 180 may use the obtained information to decide whether the user overeats.

The controller 180 may convert the decided user's body state into a numerical value related to the well driving. In this case, when the user overeats, the user's body state may be converted into a lower numerical value related to the well driving. When the user takes an appropriate amount of food, the user's body state may be converted into a higher numerical value related to the well driving. This may reflect that the user's drowsy driving probability is higher than that when the user overeats.

In some implementations, in a similar manner, the controller 180 may also convert a user's body state related to the situation in which the user takes exercise into a numerical value related to the well driving. In addition, the controller 180 may decide whether the measured exercise quantity is excessive as compared with a general statistical value or a user's average exercise quantity. In some implementations, the general statistical value may be a statistical value for measuring whether the exercise quantity is excessive based on people having body conditions similar to those of the user, including the user's age, sex, weight and the like. When the measured user's exercise quantity exceeds the general statistical value or when the measure user's exercise quantity exceeds by a predetermined level or more than a pre-calculated user's average exercise quantity, the controller 180 may decide that the user takes excessive exercise. In addition, the controller 180 may digitize the user's body state into a numerical value related to the well driving.

In some implementations, if the user's body state for each situation is converted into a numerical value related to the well driving, the controller 180 changes the numerical value related to the well driving, based on various conditions. For example, the controller 180 may allow the numerical value related to the well driving to be decreased or increased based on the lapse of time. The controller 180 may allow a numerical value related to the user's meal state to be gradually decreased until before a certain time elapses (e.g., before the user's drowsiness occurs) and then gradually increased after the certain time elapsed (e.g., after food is completely digested). Alternatively or additionally, the controller 180 may allow a numerical value related to the user's sleep state to be gradually decreased and then again increased by a predetermined level when the user has a sleep for a certain period of time, using a lunch time or the like. As such, the numerical value related to the well driving may be changed depending on a change in the user's body state.

Figure 6:
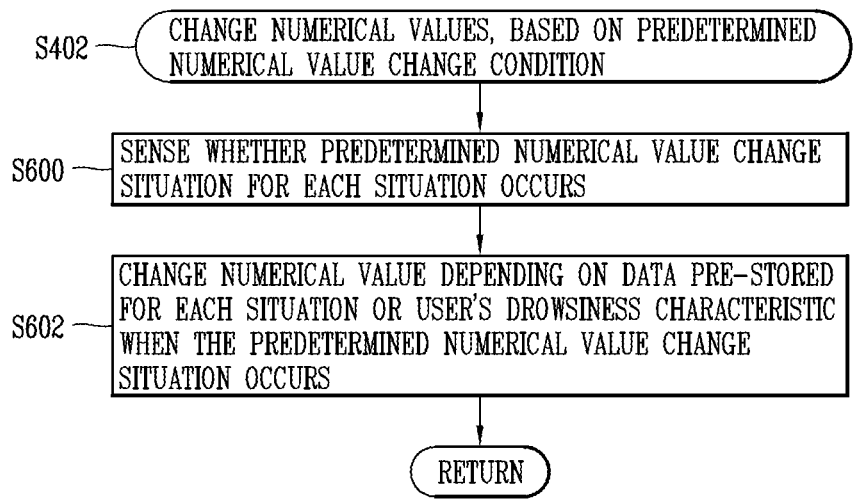
FIG. 6 is a flowchart illustrating an example of using a smart watch to change a numerical value related to a user's driving.

FIG. 6 is a flowchart illustrating an example of a process in which a numerical value related to the well driving is changed in a smart watch of a DSM system.

Referring to the example of FIG. 6, the controller 180 of the smart watch 100 senses that a predetermined numerical value change situation has occurred so that a numerical value related to the well driving is changed for each situation (S600). For example, the numerical value change situation may be a situation in which time elapses or a situation in which a predetermined numerical value related to the well driving is renewed.

In some implementations, the situation in which the numerical value related to the well driving is renewed may be a situation in which a state identical to the previously digitized user's body state again occurs, i.e., when the user has another meal (e.g., when the user has lunch after the breakfast) or when the user exercises again (e.g., when the user exercises again at lunch time after the exercise before attendance at office). Alternatively, the situation in which the numerical value related to well driving is renewed may be a situation in which the user has a short sleep of less than a predetermined time.

When the predetermined numerical value change situation occurs, the controller 180 may change the numerical value related to the well driving, determined for each situation, based on a pre-stored data or user's drowsiness characteristic (S602). For example, the controller 180 may allow the numerical value related to the well driving to be changed based on pre-stored information on a time when the drowsiness generally occurs for each situation. Here, the pre-stored information may be usually information on an average time when the drowsiness occurs after the user has a meal or takes exercise. In this case, the controller 180 may allow the numerical value related to the user's meal or exercise to be decreased for a predetermined time after the user has a meal or takes exercise.

Alternatively or additionally, the controller 180 may use information on a user's drowsiness characteristic as the pre-stored information for changing the numerical value related to the well driving. In some implementations, the user's drowsiness characteristic may be a characteristic that the user is more or less drowsy than an average statistical value, with respect to a specific situation (e.g., overeat, excessive exercise, insufficient sleep, or the like). Alternatively or additionally, the user's drowsiness characteristic may be a characteristic related to a time when the user's drowsiness occurs with respect to a specific situation.

The drowsiness characteristic may be decided based on a result obtained by measuring a state in which the user is actually drowsy. For example, in some implementations, when it is decided that the user is drowsy by obtaining a user's biological signal, the controller 180 may collect information related to the user's drowsiness characteristic, based on a currently measured user's state (e.g., an overeat state, an excessive exercise state, a sleep deprivation state, or the like), and decide the user's drowsiness characteristic, based on the collected information.

Figure 7:
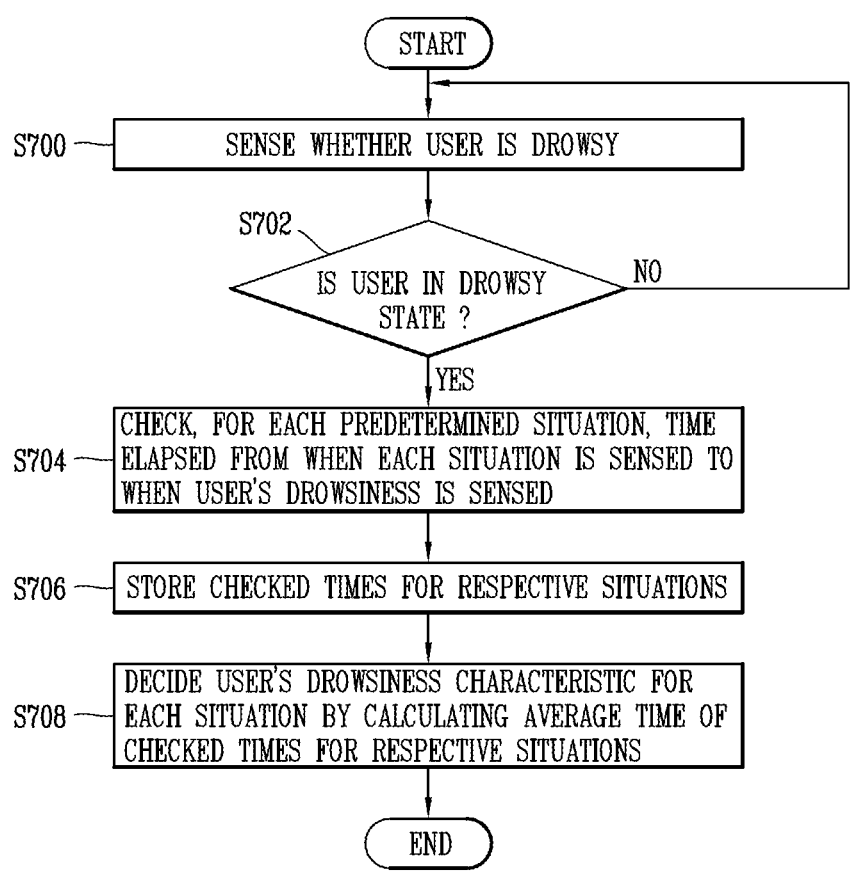
FIG. 7 is a flowchart illustrating an example of using a smart watch to determine a user's drowsiness characteristic

FIG. 7 is a flowchart illustrating details of an example of an operation process of deciding a user's drowsiness characteristic in a smart watch of a DSM system.

Referring to the example of FIG. 7, the controller 180 of the smart watch 100 determines whether the user is drowsy by sensing a user's state (S700). When it is decided in step S700 that the user is drowsy, the controller 180 checks, for each currently measured user's body state, a time elapsed from when each situation is sensed to when the user's drowsiness is sensed (S704).

As an example, if the state in which the user is drowsy is sensed, the controller 180 may check whether the user has a sleep for a certain period of time during the time elapsed after the user wakes up. The controller 180 may identify a user's meal time closest to the time when the user's drowsiness state is sensed, and measure a time elapsed until the user's drowsiness state is sensed after the user's meal time. The controller 180 may identify whether the user is in an overeat state. Alternatively or additionally, when the user takes exercise before the user's drowsiness state is sensed, the controller 180 may decide whether the user takes excessive exercise, and measure a time elapsed from when the user takes exercise to when the user's drowsiness state is started.

The controller 180 may collect these measured results as information on the user's drowsiness characteristic. In some implementations, the time from when the user has a meal to when the user's drowsiness state is started may become a drowsiness characteristic related to the user's meal state. If the user overeats, information on a drowsiness characteristic corresponding to the overeat state may be collected. In a similar manner, information on a drowsiness characteristic related to the user's exercise state (e.g., a drowsiness characteristic when the user takes excessive exercise) and a drowsiness characteristic related to the user's sleep state (e.g., a drowsiness characteristic when the user is in a sleep deprivation state) may be collected. The information collected as described above may be stored for each situation (S706), and be used as information for detecting the user's drowsiness characteristic.

In some implementations, in step S706, when the information is collected more than a predetermined amount of information, the controller 180 may calculate an average time of the elapsed times for the respective situations. The calculated average time may become, for each situation, the drowsiness characteristic when the user overeats or eats little, the drowsiness characteristic when the user is in an excessive exercise state or an exercise deprivation state, the drowsiness characteristic when the user is in a sleep deprivation state or an excessive sleep state, etc. When the user's drowsiness characteristic is decided as described above, the controller 180, in step S602, may allow the numerical value related to the well driving to be changed depending on the decided user's drowsiness characteristic.

In some implementations, the controller 180 may allow the numerical value related to a specific situation to be changed based on a time corresponding to the user's drowsiness characteristic. For example, in case of a user having a characteristic that the user is frequently drowsy when one hour elapses after the user overeats, the controller 180 may allow the numerical value related to a user's meal state to be changed by reflecting the user's drowsiness characteristic. In some implementations, when it is decided that the user is not in an overeating state, the controller 180 may allow the numerical value related to the user's meal for one hour to be continuously decreased or decreased more quickly than usual.

Although the foregoing descriptions have provided examples of the user's drowsiness characteristic related to the time when the user's drowsiness occurs and the time when a specific situation occurs, other implementations are possible. For example, the user's drowsiness characteristic may be related to the number of times that the user's drowsiness has been detected. That is, the controller 180 may sense a number of times of the user's drowsiness for a predetermined period (e.g., a day), and decide the user's drowsiness characteristic, based on the user's body state for each situation and the number of times of the user's drowsiness.

For example, when the user is in the sleep deprivation state, the controller 180 may measure a number of times of the user's drowsiness in the sleep deprivation state by measuring the number of times of the user's drowsiness for the day. Alternatively or additionally, the controller 180 may measure a number of times of the user's drowsiness in the overeat state, based on the number of times of the user's overeat state, which occurs within the predetermined period, and the number of times of the user's drowsiness. In a similar manner, the controller 180 may measure a number of times of the user's drowsiness in the excessive exercise state. The controller 180 may decide a user's state in which the user is more or less drowsy than a general statistical value, based on the result obtained by measuring the number of times of the user's drowsiness for each situation.

The controller 180 may allow the numerical value related to the well driving to be changed based on the user's drowsiness characteristic. In some implementations, when the user's body state with respect to a specific situation is decided as a user's body state in which the user is more drowsy than the general statistical value, the controller 180 may allow the numerical value related to the well driving to be decreased more quickly than the speed at which the numerical value is generally decreased. As another example, when the user's body state is decided as a user's body state in which the user is less drowsy than the general statistical value, the controller 180 may allow the numerical value related to the well driving to be decreased more slowly than the speed at which the numerical value is generally decreased.

In some implementations, the controller 180 of the smart watch 100 may repeatedly perform some processes (e.g., steps S400 and S402) when the user does not drive the vehicle. For example, when the user's body state is changed as a new situation occurs, the numerical values related to the well driving may be renewed according to the change in the user's body state. When it is sensed that the user gets on the vehicle to drive the vehicle, the controller 180 calculates a WDS, based on the numerical values related to the well driving, which have been calculated up to now. The controller 180 may estimate a user's drowsy driving possibility, based on the calculated WDS, or allow at least one predetermined drowsy driving prevention function to be performed under a user's selection, based on the estimated result.

Figure 8:
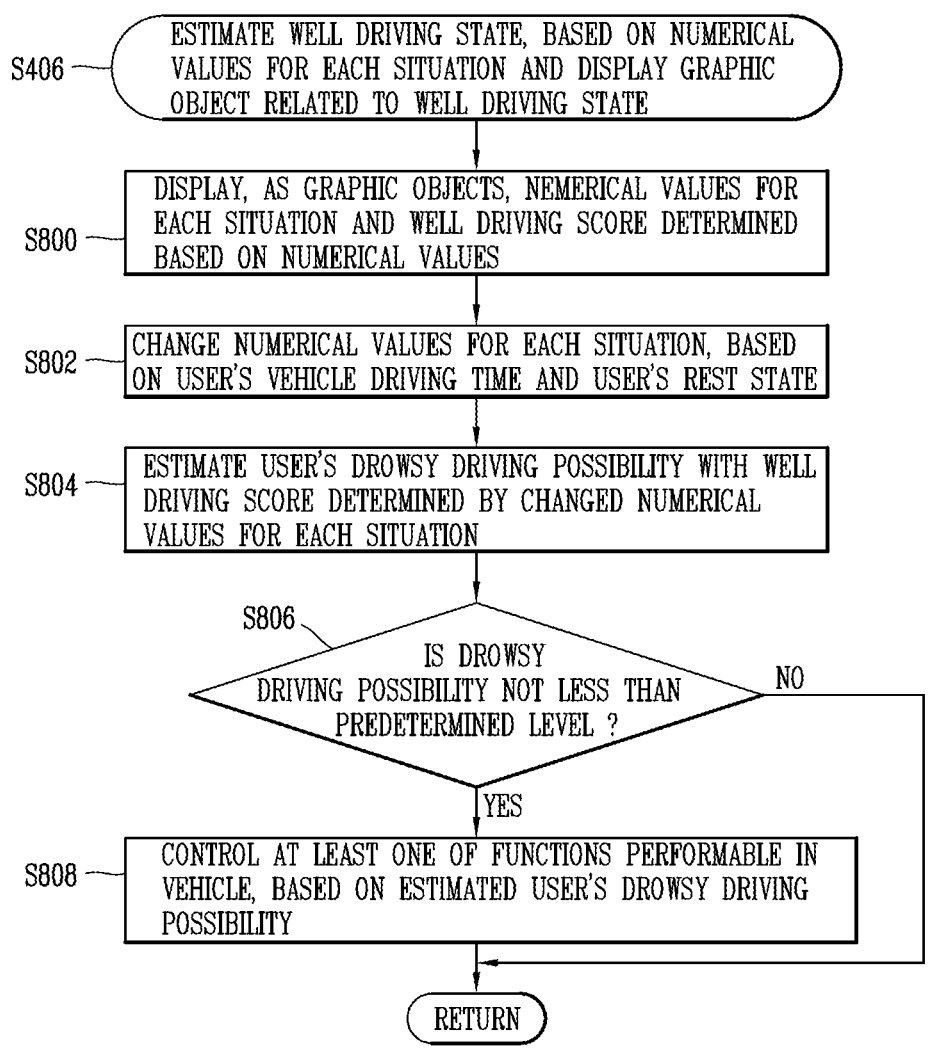
FIG. 8 is a flowchart illustrating an example of using a smart watch to estimate a user's driving state, based on numerical values obtained by estimating a user's body state.

FIG. 8 is a flowchart illustrating an example of an operation process of estimating a user's driving state, based on numerical values obtained by estimating a user's body state, in a smart watch of a DSM system.

Referring to the example of FIG. 8, if it is determined that the user drives the vehicle after getting into the vehicle, the controller 180 of the smart watch 100 may display a graphic object including a WDS as image information, based on the numerical values determined in steps S400 and S402. In some implementations, the image information may be displayed on the display unit 151 of the smart watch 100 or the display unit 300 or wind shield glass 302 provided in the vehicle.

In some implementations, in the graphic object, the numerical values related to the well driving may be displayed in forms recognizable by the user. For example, the numerical values related to the well driving may be displayed in forms having different areas according to a ratio included in the WDS, or be displayed in numbers corresponding to the ratio included in the WDS. Thus, the system may enable the user to identify numerical values related to the respective situations in the display WDS, and take an action for increasing the WDS.

In some implementations, the controller 180 may display a numerical value related to a specific situation to be distinguished from other numerical values. For example, the controller 180 may display a graphic object corresponding to the lowest numerical value among the numerical values related to the well driving to be distinguished from other numerical values, using another color or highlight indication. For example, when the user's drowsy driving possibility estimated based on the WDS is a predetermined level or more, the controller 180 displays the lowest numerical value to be distinguished from other numerical values, so that the user can recognize the greatest factor that may cause the user's drowsy driving.

In some implementations, the controller 180 may change the numerical values for each situation, based on various situations that may occur while the user is driving the vehicle (S802). For example, the numerical values related to the well driving may be gradually decreased in proportion to a driving time, by reflecting continuous accumulation of fatigue, caused as the user drives the vehicle. Alternatively or additionally, the numerical values related to the well driving may be changed based on a state in which the user takes a rest. Alternatively or additionally, the numerical values related to the well driving may be changed by reflecting a specific situation directly input from the user. Alternatively or additionally, when there is a user's drowsiness characteristic related to driving of the vehicle, the numerical values related to the well driving may be changed based on the user's drowsiness characteristic. Hereinafter, the operation process in which the controller 180 changes the numerical values related to the well driving will be described in detail with reference to FIG. 9.

In some implementations, in step S802, when the numerical values related to the well driving are changed, the WDS may be changed depending on the changed numerical values. In this case, the controller 180 may estimate a user's drowsy driving possibility, based on the changed WDS (S804). For example, the controller 180 may decide that the user's drowsy driving possibility is high as the WDS becomes low. When the WDS decreases to less than a predetermined level, the controller 180 may decide that the user's drowsy driving possibility is a predetermined level or more.

In some implementations, when it is decided in step S804 that the user's drowsy driving possibility is the predetermined level or more, the controller 180 may control at least one predetermined user's drowsy driving prevention function to be performed under a user's selection (S808). The user's drowsy driving prevention function may be a function provided in the smart watch 100 or a function using various kinds of devices provided in the vehicle to interact with the vehicle.

For example, when it is decided that the user's drowsy driving possibility is high, the controller 180 may change an environmental state of the vehicle in order to prevent the user's drowsy driving. In some implementations, the controller 180 may allow a predetermined sound source for preventing the user's drowsy driving to be reproduced, or change window of the vehicle to be opened or in a further opened state. Alternatively or additionally, the controller 180 may control an illumination inside the vehicle to be brighter or be changed as a light source of another color.

In some implementations, the environmental state of the vehicle may be changed based on pre-collected environmental setting information. For example, when the user drives the vehicle, the controller 180 may detect whether the user is in an awakened state from the obtained user's biological information. When the user drives the vehicle in the awakened state, the controller 180 may collect environmental setting information of the vehicle. When the collected environmental setting information are the same, the controller 180 may provide a weight to the corresponding environmental setting information.

As a part of the user's drowsy driving prevention function, the controller 180 may allow the environmental state of the vehicle to be changed using any one of the collected environmental setting information. For example, the controller 180 may select the environmental setting information in the order where the weight is high. When it is decided that the user does not enter into the awakened state, the controller 180 may allow the environmental state of the vehicle to be changed based on another environmental setting information. For example, the controller 180 may decide whether the user enters into the awakened state by obtaining the user's biological information. When the user enters into the awakened state, the controller 180 may provide a greater weight to the current environmental setting information of the vehicle.

Alternatively or additionally, the controller 180 may allow vibration of a predetermined pattern to be output as the user's drowsy driving prevention function. The vibration may be generated through the haptic module 153 provided in the smart watch 100, or be generated through a vibration module provided in a seat of the vehicle. In addition, the pattern of the vibration may be irregular.

As the user's drowsy driving prevention function, the controller 180 may perform a function of making a call to a predetermined number. In this case, the controller 180 may allow the user to select a person who receives a call through image information displayed on the display unit 151 or the display unit 300 or wind shield glass 302 provided in the vehicle.

In addition, as a part of the user's drowsy driving prevention function, the controller 180 may perform a function of providing navigation information on a predetermined specific point. As an example, the specific point refers to a point at which the user can take a rest for a while, and may be information on an empty lot or parking lot provided at a roadside, a resident building, or the like. Here, the user may previously set information for selecting the specific point. In this case, the controller 180 may select the specific point in the order where the shortest distance or minimum time is taken about the current position of the vehicle, based on the information set by the user, and output navigation information on the selected specific point. Here, the navigation information may be displayed through the display unit 151 or the display unit 300 or wind shield glass 302 provided in the vehicle.

In some implementations, the user's drowsy driving prevention function may be performed based on a user's selection. For example, the controller 180 may display image information related to the performance of the user's drowsy driving prevention function on the display unit 151 or the like before the user's drowsy driving prevention function is performed, and allow the user's drowsy driving prevention function to be performed only when there is a user's selection through the image information. In some implementations, the user's drowsy driving prevention function may be provided in the form of inviting or proposing the user, and be performed under a user's approval.

In some implementations, the controller 180 may set one or more steps in the performance of the user's drowsy driving prevention function, and allow different user's drowsy prevention function to be performed for the respective steps. For example, the controller 180 may divide the steps into three steps, and allow a function having a strong drowsy driving prevention effect to be performed as the WDS becomes low. In some implementations, when the WDS is slightly lower than a predetermined level (corresponding to a predetermined first step), the controller 180 may change the environmental state of the vehicle, based on any one of the pre-collected environmental setting information. However, when the WDS is further lowered (corresponding to a predetermined second step), the controller 180 may allow a function of making a call to a predetermined number to be performed as the corresponding user's drowsy driving prevention function. However, when the WDS is further lowered (corresponding to a predetermined third step), the controller 180 may allow a function of providing navigation information on a predetermined specific point to be performed.

In addition, the controller 180 may use the user's drowsiness characteristic in the decision of the user's drowsy driving possibility.

For example, the controller 180 may previously estimate a time when it is highly likely that the user may be drowsy, based on the previously detected user's drowsiness characteristic. In case of a user having a drowsiness characteristic that the user is drowsy even after driving the vehicle for one hour, the controller 180 may decide whether the user's sleep is insufficient, based on the user's sleep time. When the user's driving time exceeds one hour in the state in which the user's sleep is insufficient, the user's drowsy driving possibility may be highly estimated. Accordingly, in case of a user having the user's drowsy characteristic, the controller 180 may estimate the time when one hour is elapsed after the user's driving is started as a time when the user's drowsy driving possibility is high, and allow a predetermined user's drowsy prevention function to be performed under a user's selection at the corresponding time.

Some of the processes (e.g., steps S800 to S808) may be repeatedly performed while the user is driving the vehicle. Accordingly, when a user's state is changed (e.g., when the user takes a rest), the WDS renewed based on the changed state may be displayed as image information in step S800.

In step S802, the numerical values related to the well driving for each situation may be changed based on various situations that may occur during the user's driving of the vehicle. Here, the situation in which the numerical values related to the well driving for each situation may be varied. For example, the controller 180 may change the numerical values related to the well driving, based on time. The numerical values related to the well driving may be changed based on the previously detected user's drowsiness characteristic. Alternatively or additionally, the numerical value related to the well driving may be changed based on various situations that may occur while the user is driving the vehicle.

Figure 9:
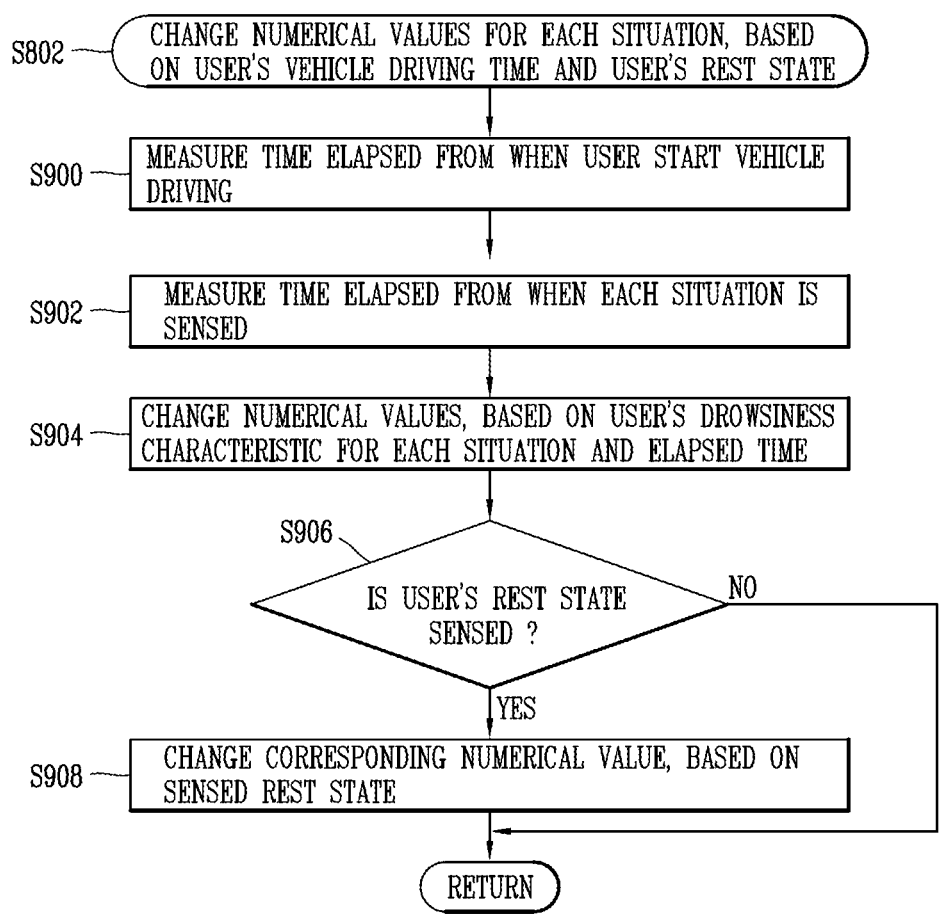
FIG. 9 is a flowchart illustrating an example of using a smart watch to change numerical values related to a user's driving, based on the user's drowsiness characteristic or an indication of sensing of a user's rest state.

FIG. 9 is a flowchart illustrating an example of a process of changing numerical values related to well driving, based on the user's drowsiness characteristic or the presence of sensing of a user's rest state, in a smart watch of a DSM system.

Referring to the example of FIG. 9, the controller 180 of the smart watch 100 may measure a time elapsed until the present time after the user's driving of the vehicle is started (S900). The controller 180 measures a time elapsed until the present time after each situation related to the numerical value is sensed (S902). The controller 180 changes the numerical value related to the well driving, based on the user's drowsiness characteristic related to the numerical value for each situation and the elapsed times measured in steps S900 and S902 (S904).

For example, when the user drives the vehicle in the state in which the user overeats, the controller 180 may determine the numerical value related to the 'meal', based on the time elapsed until the present time after the user has a meal. When the user is frequently drowsy after overeating, the controller 180 may allow the numerical number related to the 'meal' to be decreased more quickly than usual. Alternatively or additionally, if the system determines that the user is frequently drowsy after two hours are elapsed from the time when the user has a meal, the controller 180 may allow the numerical value related to the 'meal' to be decreased more quickly than usual at the time when the two hours are elapsed from the time when the user has the meal.

In addition, when the numerical values related to the well driving are changed, the controller 180 may further consider a user's drowsiness characteristic in the user's driving of the vehicle. For example, if the system determines that the user driving the vehicle is more quickly or more slowly drowsy in the overeating state, the controller 180 may change the time when the speed at which the numerical value related to the 'meal' is changed, in consideration of the user's drowsiness characteristic. Alternatively or additionally, the controller 180 may allow the numerical value related to the well driving to be decreased more quickly or more slowly, in consideration of the user's drowsiness characteristic.

In some implementations, the controller 180 may sense whether the user takes a rest (S906). When the user takes a rest, the controller 180 may change a corresponding numerical value related to the well driving, based on the user's rest (S908). For example, when the user has a sleep for a certain period of time or performs stretching at an outside of the vehicle after stopping the driving of the vehicle, the controller 180 may change numerical values corresponding to the user's sleep or stretching.

In step S906, the controller 180 may decide whether the user takes a rest that can have influence on a well driving state. In some implementations, the controller 180 may decide only the case where the user takes a rest in the state in which the user stops the driving of the vehicle as the rest state that can have influence on the well driving state. In this case, the controller 180 may change the corresponding numerical value related to the well driving by reflecting the user's rest state. The change in the user's situation that can have influence on the well driving state may be previously determined. Accordingly, the controller 180 may decide that the situation has occurred based on peripheral situations, i.e., a driving state of the vehicle, a result obtained by sensing a movement of the vehicle, user's biological information, and the like.

In some implementations, in step S908, the controller 180 may change a numerical value corresponding to the user's rest state. For example, when the user takes a rest for a certain period of time after stopping the driving of the vehicle, the controller 180 a numerical value related to the 'sleep' to be increased to a predetermined level. Alternatively or additionally, if the system detects that the user performs light stretching at an outside of the vehicle, the controller 180 may allow a numerical value related to the 'exercise' to be increased to a predetermined level. Here, the controller 180 may recognize the state in which the user performs the stretching at the outside of the vehicle by sensing a movement state of the smart watch 100.

Although some examples have been descried in which the numerical value related to a 'meal' is determined when the user drives the vehicle in the overeating state, numerical values related to other situations may be changed in a similar manner. For example, similarly to that described above, numerical values related to the 'exercise' and numerical values related to the 'sleep' may also be changed. In various situations that may affect a user's well-driving, corresponding numerical values related to the well driving may be changed in a similar manner based on changing conditions of the user.

As described above, the controller 180 of the smart watch 100 according to some implementations may change numerical values related to the well driving by further considering various situations input from the user. For example, the user may further input information on a situation in which the user gets on the vehicle, a situation in which the user is on night duty, or a specific situation of the user's body state, such as a disease. The controller 180 may change the numerical values related to the well driving by further taking into account the user's input information, and calculate a WDS, based on the changed numerical values.

As described above, some examples of the operation process of the smart watch 100 according to some implementations has been described. In the following description, an example in which image information is displayed on the display unit 151 of the smart watch 100 or the display unit 300 or wind shield glass 302 of the vehicle will be described in detail.

Figure 10A:
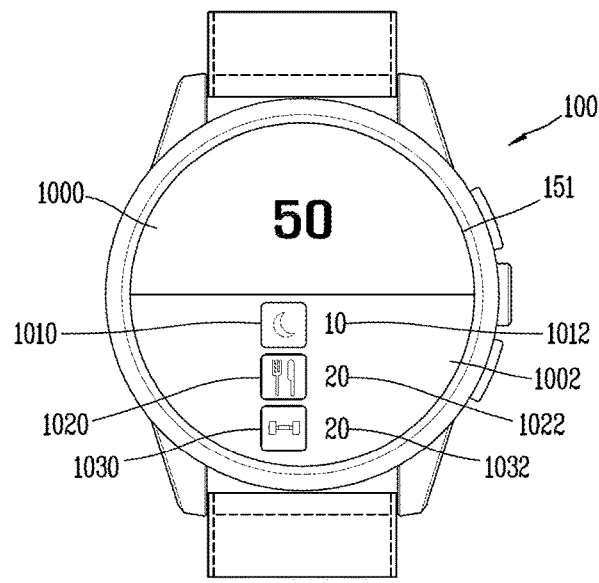
FIG. 10 is a sketch illustrating an example of displaying a well-driving score and estimated numerical values in a smart watch.
Figure 10B:
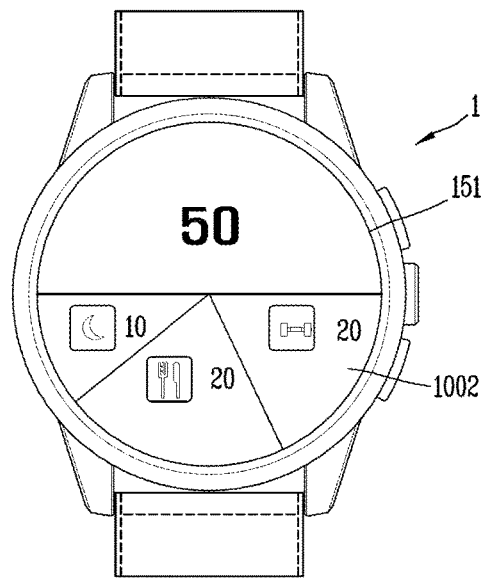
Figure 10C:
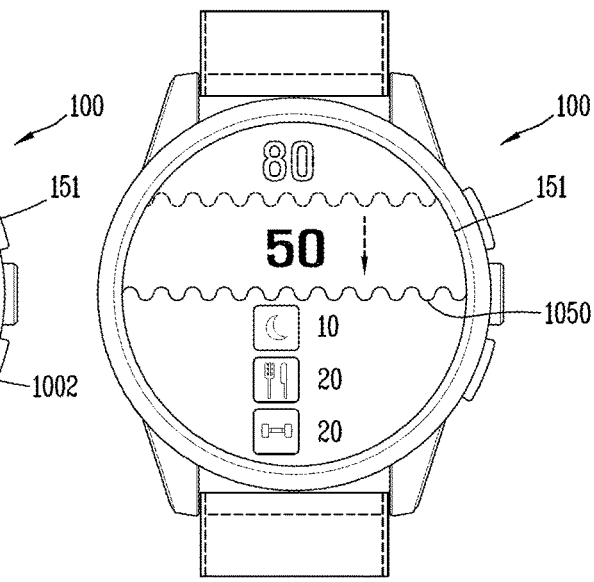

FIG. 10 is an example of a view illustrating an example in which a well driving score and estimated numerical values are displayed in a smart watch according to some implementations.

For example, based on the smart watch estimating a user's sleep, meal, and exercise states and numerical values related to the respective states and accordingly calculating a WDS, the controller 180, as shown in FIG. 10(a), may divide an area on the display unit 151 into an area 1000 for displaying the WDS and an area 1002 for displaying numerical values for each situation, and allow numerical values to be displayed in each area. The controller 180 may display numerical values 1012, 1022 and 1032 related to the well driving and graphic objects 1010, 1020 and 1030 corresponding to related situations near the respective numerical values 1012, 1022 and 1032, so that the user can recognize a numerical value related to the well driving for each situation.

Thus, if the numerical values are respectively related to user's sleep, meal and exercise states, the controller 180, as shown in FIG. 10(a), may display the graphic object 1010 related to the user's sleep state, the graphic object 1020 related to the user's meal state and the graphic object 1030 related to the user's exercise state, and display the numerical values 1012, 1022 and 1032 respectively corresponding to the graphic objects 1010, 1020 and 1030. Accordingly, in some implementations, the user can recognize the numerical values 1012, 1022 and 1032 for each situation, based on the numerical values 1012, 1022 and 1032 and the graphic objects 1010, 1020 and 1030.

In some implementations, the numerical values 1012, 1022 and 1023 for each situation or the WDS may be displayed in various forms. FIGS. 10(*b*) and 10(*c*) show such examples.

First, referring to FIG. 10(*b*), FIG. 10(*a*) shows an example in which the numerical values 1012, 1022 and 1032 are displayed in the form of graphic objects respectively having areas with different sizes according to the sizes thereof.

For example, the controller 180 may display the numerical values 1012, 1022 and 1032 in the form of graphic objects respectively having areas with different sizes in the area 1002 in which the numerical values are displayed. In this case, the areas may be displayed in different colors, and the colors may be determined based on the sizes of the respective numerical values. Thus, the user can intuitively recognize a situation related to the lowest numerical value, based on the colors and/or the areas.

FIG. 10(*c*) shows an example in which the WDS is displayed in various forms. For example, the controller 180, as shown in FIG. 10(*c*), may display the WDS as a graphic object 1050 obtained by using a state in which liquid is filled in a container. In this case, the WDS may be displayed as a level where the liquid is filled in the container. As shown in FIG. 10(*c*), the level where the liquid is filled in the container may be changed depending on a change in the WDS. Accordingly, the user can more intuitively recognize a change in the user's well driving state, based on the graphic object displaying the level where the liquid is filled.

In some implementations, the controller 180 of the smart watch 100 may perform not only image information shown in FIG. 10 but also various functions for preventing the user's drowsy driving by interacting with the vehicle.

Figure 11A:
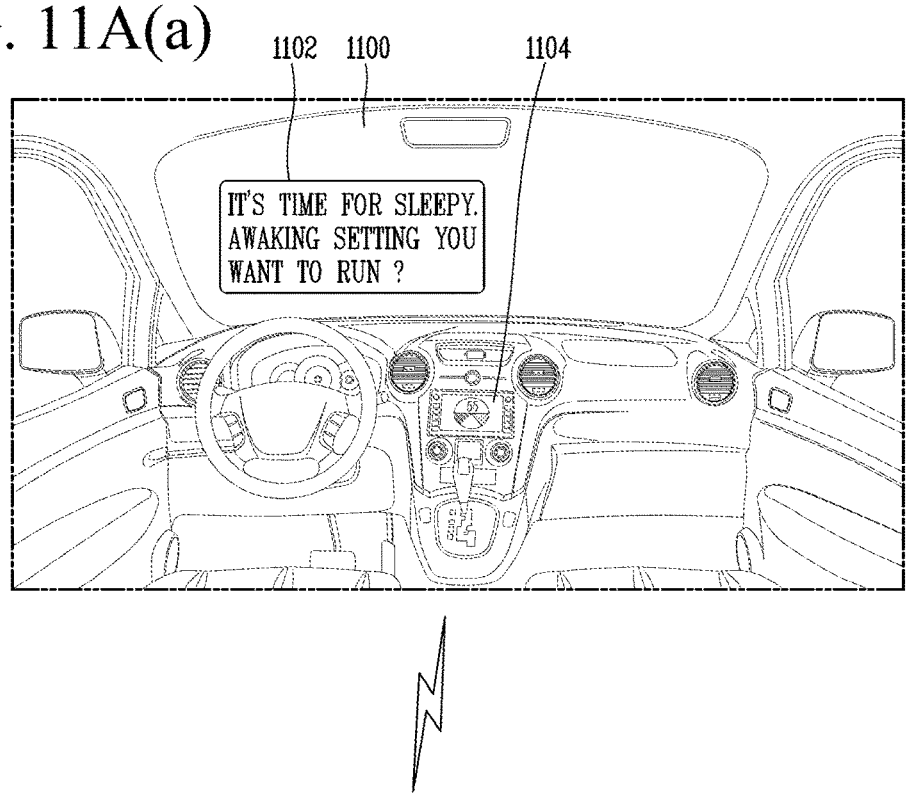
FIGS. 11A and 11B are sketches illustrating examples of a smart watch operating in conjunction with a vehicle.
Figure 11A:
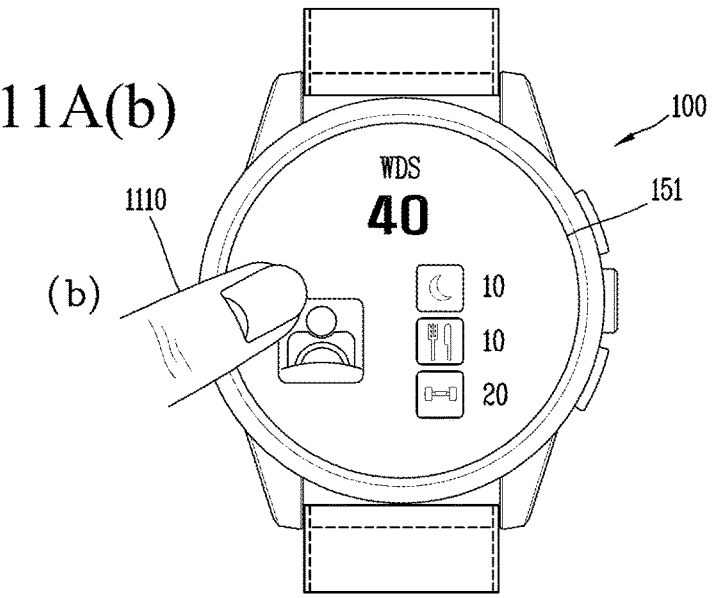
Figure 11B:
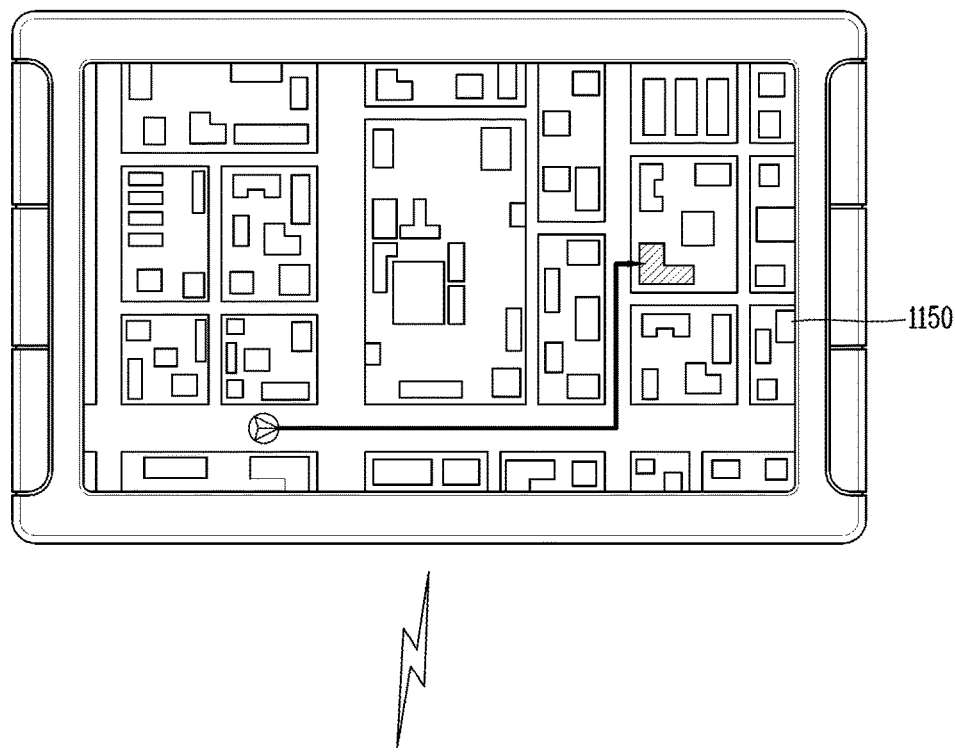
Figure 11B:
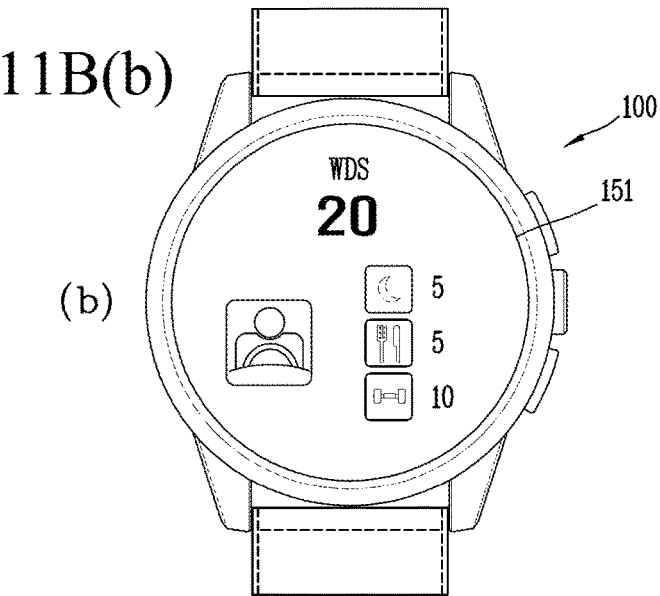

FIGS. 11A and 11B are views illustrating an example in which a smart watch operates by interacting with a vehicle according to some implementations.

For example, the controller 180 of the smart watch 100 may estimate a user's drowsy driving probability, based on a WDS, and perform various functions for preventing the user's drowsy driving.

FIG. 11A illustrates an example in which an environmental setting information of the vehicle is changed as an example of the user's drowsy driving prevention function. For example, as shown in FIG. 11A(a) before the function of changing the environmental setting function of the vehicle is performed, the controller 180 may display image information 1102 to be selected by the user. For example, the image information 1102, as shown in FIG. 11A(a), may be displayed in the HUD scheme through a wind shield glass 1100 of the vehicle. Alternatively or additionally, the image information 1102 may be displayed on a predetermined display unit 1104.

In some implementations, the user may allow the currently selected drowsy driving prevention function to be performed by inputting a user's selection with respect to the image information. For example, the user's input, as shown in FIG. 11A(b), may be a user's touch input 1110 with respect to the display unit 151 of the smart watch 100. Alternatively or additionally, the user's input may be the image information 1102 displayed on the wind shield glass 1100 or a touch input with respect to the display unit 1104 provided in the vehicle.

If the user's input is sensed, the controller 180 may perform a user's drowsy driving prevention function. For example, the controller 180, as shown in FIG. 11A(a), may perform a function of changing an environment of the vehicle into a specific environmental setting state (awaking setting). Alternatively or additionally, the controller 180 may perform a function of making a call to a specific telephone number or outputting a predetermined irregular vibration. Alternatively or additionally, the controller 180 may perform a function of providing navigation information on a predetermined point at which the user can take a rest.

In some implementations, these functions may be determined depending on the level of a user's drowsy driving possibility. For example, the user's drowsy driving possibility may be determined based on a currently calculated WDS. Therefore, when the WDS is lower than that of '40' shown in FIG. 11A(b), the function selected to prevent the user's drowsy driving may be changed.

FIG. 11B shows such an example.

For example, when the WDS is further lowered as shown in FIG. 11B(b), the controller 180 may determine that the user's drowsy driving probability becomes higher, and accordingly perform a user's drowsy driving prevention function. FIG. 11B(a) is an example of the user's drowsy driving prevention function selected in this case, and shows that the function of providing navigation information 1150 on a predetermined point at which the user can take a rest is performed.

The navigation information 1150, as shown in FIG. 11B(a), may be output through the display unit 1104 provided in the vehicle. However, the navigation information 1150 may be displayed in the HUD scheme through the wind shield glass 1100 of the vehicle. Alternatively or additionally, the navigation information 1150 may be displayed on the display unit 151 of the smart watch 100.

In addition, the function shown in FIG. 11B(a) may also be provided only when there is a user's selection. For example, like the image information 1102 shown in FIG. 11A(a), image information where the performance of a corresponding function can be selected from the user may also be displayed on the display unit 1104 provided in the vehicle or the wind shield glass 1100 of the vehicle. The function may be performed on when there is a user's response to the image information. The user's response may be performed as a user's touch input with respect to the smart watch 100.

FIG. 12 is a sketch illustrating an example in which a smart watch displays information on user's driving states collected for a predetermined time according to some implementations.

When the user ends driving of the vehicle, the controller 180 of the smart watch 100 may sense the end of the driving of the vehicle and store a result obtained by measuring a user's state change during the driving of the vehicle. In some implementations, the state change may be a result obtained by measuring a user's biological signal and/or information on a state in which the WDS is changed. When there is a user's request, the controller 180 may display the changed WDS and/or the measured result on the display unit 151 of the smart watch 100 or the display unit 300 or wind shield glass 302 provided in the vehicle.

Figure 12A:
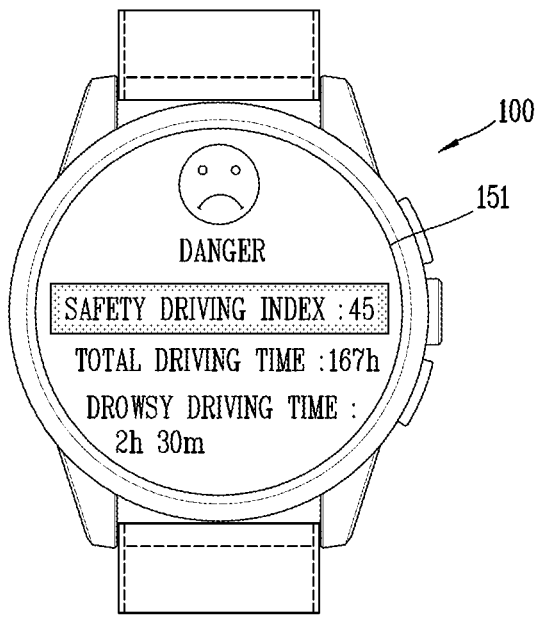
FIG. 12 is a sketch illustrating an example of using a smart watch to display information regarding a user's driving states collected for a predetermined time.

The controller 180 may provide information related to a time when the user drives the vehicle in a drowsy state by collecting the stored information for a predetermined period so that the user can be awakened. FIG. 12(a) shows an example in which a drowsy driving time for the predetermined period and a safety driving time calculated based on the drowsy driving time are displayed as image information.

Figure 12B:
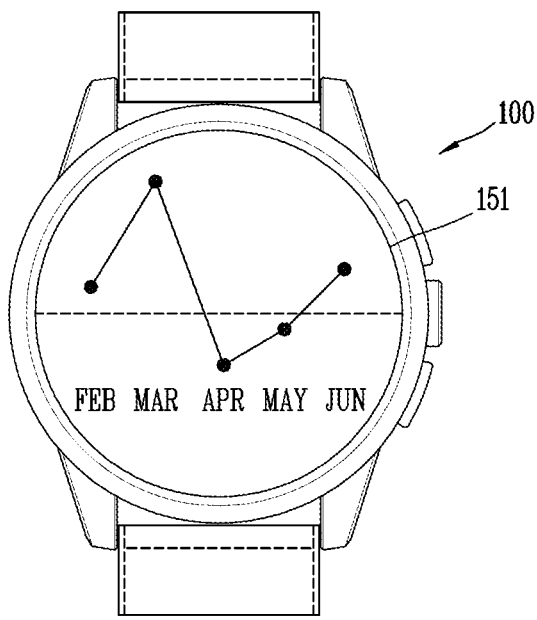

In addition, the controller 180 may provide information obtained by analyzing the collected information for each predetermined period, i.e., each week or month. Alternatively or additionally, the controller 180 may provide information obtained by analyzing a number of times of the user's drowsy driving or a case where the user's drowsy driving possibility is a predetermined level or more even though the user drives the vehicle without falling asleep for each predetermined period. FIG. 12(b) shows such an example.

Various implementations may be implemented using a machine-readable medium having instructions stored thereon for execution by a processor to perform various methods presented herein. Examples of possible machine-readable mediums include HDD(Hard Disk Drive), SSD (Solid State Disk), SDD(Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the wearable device.

The foregoing implementations and advantages are merely examples and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of some implementations described herein may be combined in various ways to obtain additional and/or alternative implementations.

As the present features may be embodied in several forms without departing from the characteristics thereof, it should also be understood that the above-described implementations are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

The methods, techniques, systems, and apparatuses described herein may be implemented in digital electronic circuitry or computer hardware, for example, by executing instructions stored in tangible computer-readable storage media.

Apparatuses implementing these techniques may include appropriate input and output devices, a computer processor, and/or tangible computer-readable storage media storing instructions for execution by a processor.

A process implementing techniques disclosed herein may be performed by a processor executing instructions stored on a tangible computer-readable storage medium for performing desired functions by operating on input data and generating appropriate output. Suitable processors include, by way of example, both general and special purpose microprocessors. Suitable computer-readable storage devices for storing executable instructions include all forms of non-volatile memory, including, by way of example, semiconductor memory devices, such as Erasable Programmable Read-Only Memory (EPROM), Electrically Erasable Programmable Read-Only Memory (EEPROM), and flash memory devices; magnetic disks such as fixed, floppy, and removable disks; other magnetic media including tape; and optical media such as Compact Discs (CDs) or Digital Video Disks (DVDs). Any of the foregoing may be supplemented by, or incorporated in, specially designed application-specific integrated circuits (ASICs).

Although the operations of the disclosed techniques may be described herein as being performed in a certain order and/or in certain combinations, in some implementations, individual operations may be rearranged in a different order, combined with other operations described herein, and/or eliminated, and desired results still may be achieved. Similarly, components in the disclosed systems may be combined in a different manner and/or replaced or supplemented by other components and desired results still may be achieved.

What is claimed is:

1. A driver state monitoring (DSM) system configured to interact with a vehicle, the DSM system comprising:
a wearable device comprising a main body configured to be worn by a user;
a display unit disposed in the main body;
an information collection unit disposed in the main body and configured to collect information related to a body state of the user; and
a controller disposed in the main body and configured to:
sense a plurality of situations associated with the user's body state based on the collected information;
for each of the sensed plurality of situations, determine body states of the user based on the collected information;
digitize the determined body states of the user into a plurality of numerical values that respectively represent the determined body states of the user corresponding to each sensed situation, based on a plurality of pre-stored information for the sensed plurality of situations associated with different body states of the user;
determine whether the vehicle connected to the wearable device is in a state of being driven;
based on a determination that the vehicle being in the state of being driven, calculate a well-driving score for the user based on a sum of the numerical values that respectively represent the determined body states of the user corresponding to each sensed situation before the user driving the vehicle; and
based on the user driving the vehicle, control at least one of the display unit or an image information output device disposed in the vehicle to display the well-driving score and the numerical values that respectively represent the determined body states of the user corresponding to each sensed situation,
wherein the plurality of pre-stored information for the sensed plurality of situations comprises information including a user's average sleep time corresponding to an average of durations of sleep of the user, information including a user's average meal size, and information including a user's average exercise quantity.

2. The DSM system of claim 1,
wherein, the controller is further configured to:
based on a determination that the sensed situation corresponds to any one of the user sleeping, the user having a meal, or the user exercising, compare the collected information to the pre-stored plurality of information,
based on a result of the comparison of the collected information to the pre-stored plurality of information, determine whether a duration of sleep of the user, a size of the meal of the user, or a quantity of exercise of the user corresponds to (i) an excessive state in which the duration of sleep of the user, the size of the meal of the user, or the quantity of exercise of the user is greater than the user's average sleep time, average meal size, or average exercise quantity, respectively, or (ii) an insufficient state in which the duration of sleep of the user, the size of the meal of the user, or the quantity of exercise of the user is less than the user's average sleep time, average meal size, or average exercise quantity, respectively, and digitize any one of the determined body states of the user corresponding to the one of the user sleeping situation, the user having the meal, or the user exercising, into (i) a first numerical value based on a determination that the duration of sleep of the user, the size of the meal of the user, or the quantity of exercise of the user corresponds to the excessive state, and (ii) a second numerical value based on a determination that the duration of sleep of the user, the size of the meal of the user, or the quantity of exercise of the user corresponds to the insufficient state, the second numerical value being different from the first numerical value.

3. The DSM system of claim 2, wherein the plurality of pre-stored information for the sensed situation further includes information based on a driving behavior of the user corresponding to the body state of the user.

4. The DSM system of claim 2, wherein the plurality of pre-stored information further includes previously collected information regarding an average sleep duration, an average meal size, or an average exercise quantity of a person whose age is within a predetermined range of an age of the user, or whose body information is within a predetermined range of one of the user's average sleep time, the user's average meal size, or the user's average exercise quantity, and wherein the controller is further configured to:
determine an existence of information obtained by measuring the user's average sleep time, the user's average meal size and the user's average exercise quantity exist; and based on determining the existence of information obtained by measuring the user's average sleep time, the user's average meal size and the user's average exercise quantity exist, converting the user's body state into each numerical value based on the previously collected information or based on the measured information.

5. The DSM system of claim 2, wherein the controller is further configured to change the numerical values corresponding to the determined body states of the user according to a drowsiness characteristic of the user that is previously determined.

6. The DSM system of claim 5, wherein the controller is further configured to, based on detecting a user's drowsy state,
collect information regarding, for each of a plurality of situations, a time from when the situation has ended to when the user's drowsy state is detected, and
determine the drowsiness characteristic of the user for each situation by measuring an average duration time for each situation.

7. The DSM system of claim 6, wherein the controller is further configured to perform at least one predetermined function for preventing the user's drowsy driving, the function including changing an environmental state of the vehicle to a particular setting among a plurality of settings that are indicated in pre-collected setting information, wherein the pre-collected setting information includes environmental setting information of the vehicle that was collected based on the controller determining that the user was driving the vehicle in an awakened state.

8. The DSM system of claim 7, wherein, the controller is further configured to:
determine whether the user's body state is converted into the awakened state subsequent to the environmental state of the vehicle being changed to the particular setting, and
based on determining whether the user's body state is converted into the awakened state subsequent to the environmental state of the vehicle being changed to the particular setting, change the environmental state of the vehicle to another setting or to indicate a weight of the particular setting in the pre-collected setting information.

9. The DSM system of claim 8, wherein the controller is further configured to change the environmental state of the vehicle to another setting by selecting a setting from the pre-collected environmental setting information in order of highest weight.

10. The DSM system of claim 1, wherein the controller is further configured to:
determine whether the user is in a rest state based on a state of the vehicle, and
based on determining that the user is in the rest state, change a numerical value corresponding to the rest state of the user among the plurality of values.

11. The DSM system of claim 1, wherein the controller is further configured to:
based on a determination whether the well-driving score is less than a predetermined level, estimate whether a user's drowsy driving probability is greater than a threshold, and
based on an estimation result of whether the user's drowsy driving probability is greater than the threshold, perform at least one of predetermined functions for preventing the user's drowsy driving.

12. The DSM system of claim 1, wherein the controller is further configured to display, on the display unit and based on determining that the driving of the vehicle is ended, a result obtained by measuring a change in the user's body state during driving of the vehicle, and
wherein the change in the user's body state is measured based on sensing a biological signal of the user.

13. The DSM system of claim 1, wherein the information collection unit is further configured to collect information related to the user's body state from a peripheral device that is external to the DSM system.

14. The DSM system of claim 1, where the information collection unit is further configured to collect environmental information regarding the vehicle.

15. A method for controlling a driver state monitoring (DSM) system capable of interacting with a vehicle, the method comprising:
collecting, by a wearable device worn by a user, environmental information around the wearable device;
sensing, by the wearable device, a plurality of situations of the user based on the collected environmental information;
for each of the sensed plurality of situations, determining body states of the user that respectively represent the sensed plurality of situations of the user based on the collected environmental information;
digitizing the determined body states of the user into a plurality of numerical values that respectively represent the determined body states of the user corresponding to each sensed situation, based on a plurality of pre-stored information for the sensed plurality of situations associated with the body states;
determining whether the vehicle connected to the wearable device is in a state of being driven;
based on a determination that the vehicle being in the state of being driven, calculating a well-driving score for the user based on a sum of the numerical values that respectively represent the determined body states of the user corresponding to each sensed situation before the user driving the vehicle; and
based on the user driving the vehicle, controlling at least one of a display unit or an image information output device to display the well-driving score and the plurality of numerical values that represent the body states of the user corresponding to each sensed situation,
wherein the plurality of pre-stored information for the sensed plurality of situations comprises information including a user's average sleep time corresponding to an average of durations of sleep of the user, information including a user's average meal size, and information including a user's average exercise quantity.

16. A vehicle comprising:
a driver state monitoring (DSM) system configured to perform operations that include:
  sensing, by a wearable device worn by a user, a plurality of situations of the user based on environmental information around the user;
  collecting, by the wearable device, information related to a body state of the user;
  for each of the sensed plurality of situations, determining body states of the user that respectively represent the sensed plurality of situations of the user based on the collected information related to the body state of the user;
  digitizing the determined body states of the user into a plurality of numerical values that represent respectively corresponds to the determined body states of the user corresponding to each sensed situation, based on a plurality of pre-stored information for the sensed plurality of situations;
  determining whether the vehicle connected to the wearable device is in a state of being driven;
  based on a determination that the vehicle being in the state of being driven, calculating a well-driving score for the user based on sum of the numerical values that respectively represent the body states of the user corresponding to each sensed situation; and
  based on the user driving the vehicle, controlling at least one of a display unit or an image information output device to display the well-driving score and the plurality of numerical values that respectively represent the determined body states of the user,
wherein the plurality of pre-stored information for the sensed plurality of situations comprises information including a user's average sleep time corresponding to an average of durations of sleep of the user, information including a user's average meal size, and information including a user's average exercise quantity.

* * * * *